Figure 1:
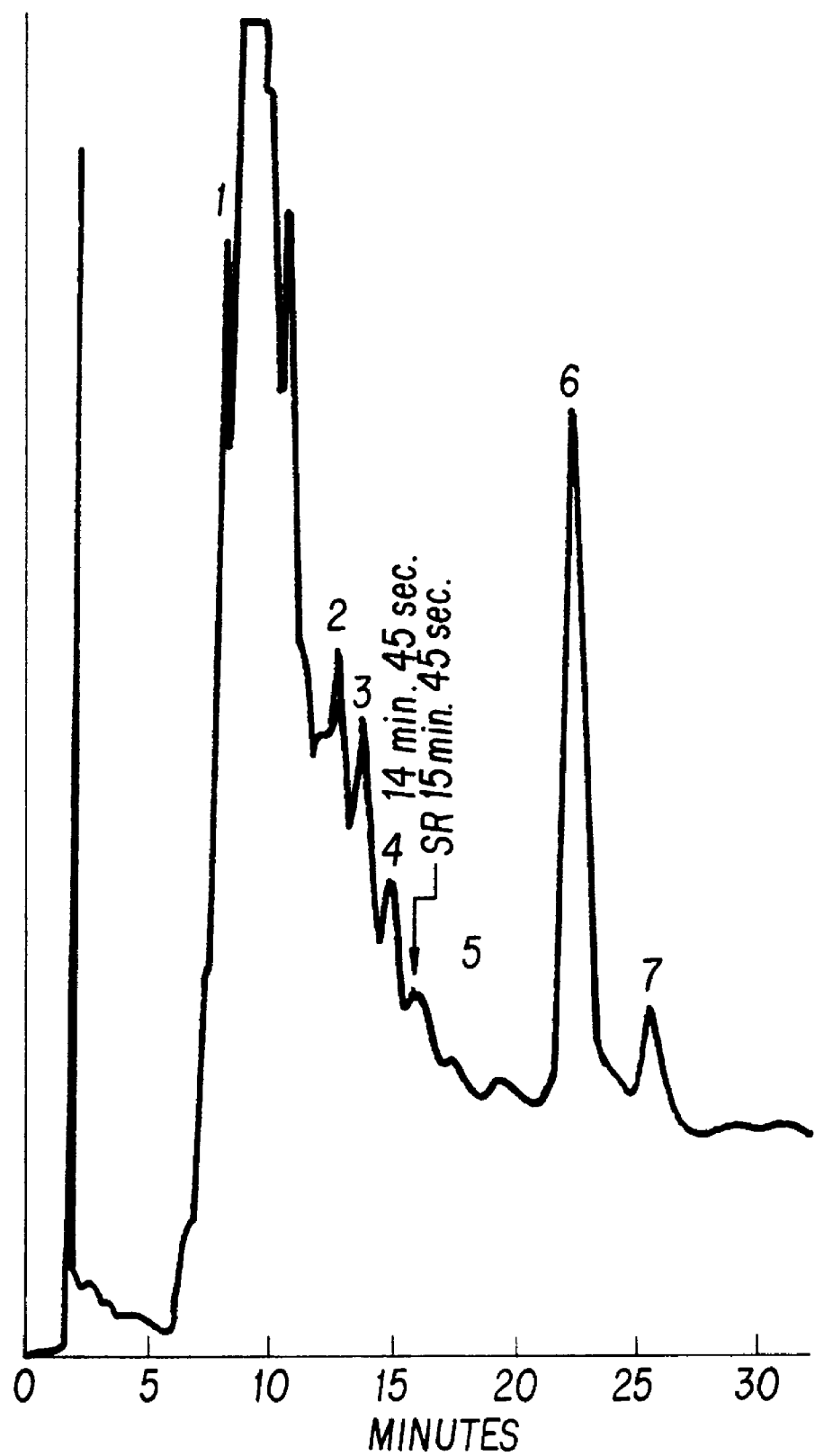

United States Patent [19]
Strobel et al.

[11] Patent Number: 5,837,685
[45] Date of Patent: *Nov. 17, 1998

[54] PEPTIDES FROM *PSEUDOMONAS SYRINGAE* POSSESSING BROAD-SPECTRUM ANTIBIOTIC ACTIVITY

[75] Inventors: Gary A. Strobel, Bozeman, Mont.; Leslie A. Harrison, Chesterfield, Mo.; David B. Teplow, Waban, Mass.

[73] Assignee: Research and Development Institute Inc. at Montana State University, Bozeman, Mont.

[*] Notice: The term of this patent shall not extend beyond the expiration date of Pat. No. 5,576,298.

[21] Appl. No.: 673,775

[22] Filed: Jun. 27, 1996

Related U.S. Application Data

[63] Continuation of Ser. No. 305,943, Sep. 15, 1994, Pat. No. 5,576,298, which is a continuation-in-part of Ser. No. 982,687, Nov. 30, 1992, abandoned.

[51] Int. Cl.$^6$ ..................................................... A61K 38/12
[52] U.S. Cl. .................................. 514/15; 514/2; 514/11; 530/300; 530/317; 435/252.34
[58] Field of Search ................................... 514/11, 15, 2; 530/328, 317, 300; 435/252.34

[56] References Cited

U.S. PATENT DOCUMENTS 5,576,298  11/1996  Strobel et al. ............................. 514/15

OTHER PUBLICATIONS

Master's Thesis, Harrison, Leslie, Montana State University, pp. 1–61, Oct. 1, 1990.
"Relevance of a chlorine substituent for the antifungal activity . . . ", Grgurina, I., et al., Experientia, vol. 50., No. 2, 1994, pp. 130–133.

"Novel bioactive lipodepsipeptides from *Pseudomonas syringae:* the pseudomycins", Ballio, A., et al., FEBS Letters 355 (1994), 96–100.

"Structure of syringotoxin, a bioactive metabolite of *Pseudomonas syringae* pv. *syringae*", Ballio, a., et al., FEBS Letters 269 (1990) 377–380.

"Structural Studies on Syringomycin", Segre, A., et al., Phytotoxins and Plant Pathogenesis, 1989, 367–371.

"Structure of Phytotoxin Syringomycin Produced by a Sugar Cane Isolate of *Pseudomonas syringae* pv. *syringae*", Fukuchi, N., et al., Tetrahedron Letters 31, 1990, 1589–92.

"Structure and Stereochemistry of Three Phytotoxins . . . ," Fukuchi, N., et al., J. Chem. Soc. Perkin Trans. 1 (1992), (9), 1149–57.

"Isolation and Structural Elucidation of Syringostatins, . . . ", Fukuchi, N., et al., J. Chem. Soc. Perkin Trans. 1, (1992), (7), 875–880, "Pseudomycins, a family of novel peptides from *Pseudomonas syringae* possessing broad–spectrum antifungal activity", Harrison et al., *Journal of Microbiology*, pp. 2857–2865, 1991.

*Primary Examiner*—David Lukton
*Attorney, Agent, or Firm*—Lowe, Price, LeBlanc & Becker

[57] ABSTRACT

Peptide antimycotics, termed pseudomycins, display broad spectrum antibiotic activity, and in particular are highly effective, non-toxic antibiotics against fungal pathogens of human and animal disease. The peptide antimycotics (pseudomycins) may be used in the treatment of the fungal pathogen *Candida albicans*. Also disclosed is a method of purification and isolation, including characterization, of the pseudomycins.

19 Claims, 15 Drawing Sheets

PEPTIDES FROM *PSEUDOMONAS SYRINGAE* POSSESSING BROAD-SPECTRUM ANTIBIOTIC ACTIVITY

This application is a continuation of application Ser. No. 08/305,943 filed Sep. 15, 1994, now U.S. Pat. No. 5,576, 298, issued Nov. 19, 1996, which is a continuation-in-part of application Ser. No. 07/982,687, filed Nov. 30, 1992, now abandoned, the entire contents of each of which are incorporated herein by reference.

This invention was made with support of grant numbers DMB 8607347 and DIR 18937 awarded by the National Science Foundation.

TECHNICAL FIELD

The present invention relates to peptide antimycotics, termed pseudomycins, which display wide spectrum antibiotic activity, and in particular are highly effective, non-toxic antibiotics against fungal pathogens of human and animal disease. In a preferred embodiment, the peptide antimycotics (pseudomycins) according to the present invention are particularly useful in the treatment of the fungal pathogen *Candida albicans*. The peptide antimycotics (pseudomycins) are also effective in the treatment of plant disease and may additionally be used as herbicides.

The present invention also relates to the method of purification and isolation, including characterization, of the peptide antimycotics (pseudomycins).

BACKGROUND OF THE INVENTION

Fungi adversely affect the health and well being of mankind in numerous ways. The most direct of these ways include a variety of disease processes affecting humans, such as opportunistic infections in immunologically compromised patients, such as patients afflicted with AIDS. The most common treatment currently available for these fungal infections is administration of the antibiotic amphotericin B. However, this compound is highly toxic and doses must be kept to a minimum, especially in critically ill patients. Doses are thus often in amounts insufficient to cure the disease or even halt the infection.

Other harmful effects of fungi include the adverse economic and social effects of plant disease. Purified natural herbicides have at least two advantages; 1) as weed control agents they have longer shelf life, wider range of storage conditions, a broader environmental window for application, less storage space, and a greater ease of application than with living organisms and 2) new microbial phytotoxins may be useful in expanding the number of sites of action of herbicides, in that there is little overlap between the known sites of action of commercial herbicides and of microbially-produced phytotoxins.

*Pseudomonas syringae* represents a wide range of plant-associated bacteria, some of which are pathogens, while others are weak pathogens or saprophytes. Many biotypes of *P. syringae* produce one or more bioactive substances that may allow the bacterium to survive in its niche; for instance, on a leaf surface where it must compete with fungi and other bacteria.

A number of novel strategies for the biological control of fungal plant diseases have been developed based on this observation. For example, a transposon-generated regulatory mutant of the wild-type strain of *P. syringae* 174 (MSU 16H) has been isolated that in culture produces increased zones of fungal inhibition when compared to the wild-type bacterium.

*Pseudomonas syringae* MSU 16H is a transposon-generated mutant of a wild-type strain that has attracted interest for its ability to make in culture elevated amounts of antifungal metabolites and to confer a greater protection than the wild-type strain in elms infected with *Ceratocystic ulmi*, the causal agent of Dutch elm disease (Lam et al., (1987) Proc. Natl. Sci. USA 84, 6447–6451). It was tested in elms and shown to confer a greater protective effect than the wild-type strain. More extensive tests on field-grown elms have confirmed the phenomenon of biocontrol at the prophylactic level.

Recently those metabolites, called pseudomycins, have been isolated and their structures have been partially characterized (Harrison et al., (1991), J. Gen. Microbiol. 137, 2857–2865).

Identification of the chemical nature of such toxins, however, has been very limited. Prior to 1970 no correct toxin structure had been published. More recently, attempts have been made to isolate and characterize the molecules responsible for the antimycotic activity of *P. syringae* MSU 16 H. However, none have been successful because the bioactivity has not been preserved.

The present inventors isolate the complete structure of pseudomycins A, B, C and C'. They are new lipodepsinonapedtides related to syringomycins (Segre et al. (1989) FEBS Lett. 255, 27–31; and Fukuchi et al. (1990) Tetrahedron Lett. 31:1589–1592), syringotoxin (Ballio et al. (1990) FEBS Lett. 269; 377–380; and Fukuchi et al. (1990) Agric. Biol. Chem. 54; 3377–3379) and syringostatins (Isogai et al. (1990) Tetrahedron Lett. 31, 695–698), a group of antimicrobial compounds produced by different isolates of *P. syringae* pv. *syringae*.

The inventors show that pseudomycins D and D' are identical to syringopeptin $SP_{25}$-A and $SP_{25}$-D respectively, lipodepeipeptides with 25 amino acid residues produced by some isolates of *P. syringae* pv. *syringae* (Ballio et al. (1991) FEBS Lett. 291: 109–112).

SUMMARY OF THE INVENTION

In accordance with the present invention, it has been discovered that the peptide antimycotics (pseudomycins) prepared according to the present invention possess broad spectrum antibiotic activity and have numerous applications. In particular, it has been unexpectedly found that the peptide antimycotics of the present invention have significant antimycotic activity especially useful for the treatment of human or animal fungal pathogens.

Furthermore, it has been discovered that the pseudomycins are surprisingly non-toxic and may be used in therapeutic doses effective not only to achieve stasis but to exterminate the fungal organism in humans or animals. In particular, the peptidyl phytotoxin exhibits inhibitory activity against fungal pathogens such as *Candida albicans, Candida tropicalis, Cryptococcus neoformans, Bipolaris spicifera* and *Aspergillus fumigatus*. The peptidyl phytotoxin is especially effective against *Candida albicans*. These human fungal pathogens cause opportunistic infections in immunologically compromised patients, such as those suffering from AIDS. Very low doses are effective against the fungal pathogens, and the pseudomycin is essentially non-toxic.

Generally, for surface infections, pseudomycin may be applied in a cream or lotion and applied to the affected area. For deep systemic infections, it is preferred that the pseudomycins be injected intravenously.

Further in accordance with the present invention, it has been unexpectedly discovered that successful purification of pseudomycins may be accomplished by the elution of pseudomycins from a C-8 HPLC column with t-propanol in trifluoro acetic acid (TFA) as the eluant. Surprisingly, this did not appreciably decrease the activity of the compound. TFA is used to preclude degradation of the pseudomycins. TFA also functions as an ion pairing agent, and the use of a gradient rather than an isocratic system substantially reduces retention times.

The purification of pseudomycins allowed the acquisition of accurate mass spectrometry data and amino acid analysis. The result is the identification of a novel peptidyl toxin produced by *Pseudomonas syringae* MSU 16H. Pseudomycins are three different peptides, pseudomycin A, pseudomycin B and pseudomycin C, each having a molecular weight of 1224, 1208 and 1252 Da, respectively. Pseudomycins A–C comprise Asx, Ser, Arg, Dab and Lys in integer molar ratios of 1:1:1:3:1. (See Table 20.) To obtain the ratios, the data are reduced to integral values based on what could possibly be allowed by the molecular weights as determined by two independent mass spectral methods—FAB and time of flight mass spectroscopy. Syringomycin differs substantially from pseudomycin in amino acid composition. If one allows for the value of 11–15 as the integral value for 1 residue per mole of pseudomycin or syringomycin, then 36–40 would represent 3 residues (as per diaminobutyric acid). Thus, only nine residues are allowed per total molecule of pseudomycins A, B, or C and syringomycin. This is based on the fact that the molecular weights of these substances is Ca 1200. Nine residues would bring the total contribution of the amino acid component to 1000. This difference is contributed by a fatty acid residue. The data of Table 20 show the fact that pseudomycins differ from syringomycin by the lysine and aspartic acid contents. The integral ratios assigned allow for only the residue number placed in parenthesis and no other value.

Thus, it is an object of the present invention to prepare treatment methods and formulations comprising peptide antimycotics, termed pseudomycins, for the treatment of human and animal pathogens.

It is a further object of the present invention to develop a method of purification for the peptide antimycotics or pseudomycins.

In particular, it is an object of the present invention to develop a purification scheme which is simple and efficient and results in high yields of active pseudomycin.

It is yet another object of the present invention to develop a method of enhancing the growth characteristics of *P. syringae* and its toxin production.

Further, it is an object of the present invention to chemically characterize and identify pseudomycins.

It is yet another object of the present invention to prepare compounds effective in the treatment of plant disease or effective as use as herbicides.

BRIEF DESCRIPTION OF DRAWINGS

Reference is now made to the drawings accompanying the application wherein:

FIG. 1 is a RP-HPLC elution profile of partially purified pseudomycin from the Amberlite XAD-2 column.

FIG. 2 is a RP-HPLC elution profile of pseudomycin run on a linear gradient of 0–80% acetonitrile over 20 minutes.

FIG. 3 shows thin layer chromatography of pseudomycin.

FIG. 4 shows FAB mass spectra of purified pseudomycin B (M+H=1208).

FIG. 5 shows $^{1}$H-NMR spectrum of pseudomycin.

FIG. 6 is a spectrophotometric scan of pseudomycin dissolved in 0.1% TFA.

FIG. 7 is a growth curve for *P. syringae* 16H grown in still culture in PDB and shake culture in mDyes medium.

FIG. 8 shows HPLC purification of pseudomycins A–D including a composite chromatograph of the four single peaks in the second run at inset.

FIG. 9 shows CE of syringomycin and pseudomycins.

FIG. 10 is an analysis of Dab and Phe by CE.

FIG. 11 shows Reverse phase HPLC of a *P. syringae* MSU 16H extract partially purified produced an elution pattern of the same type observed with syringomycin and syringotoxin-producing strains.

FIG. 12 shows the complete structure of pseudomycin A.

FIGS. 13 and 14 show the complete chemical formula and molecular structure of pseudomycin A.

FIG. 15 shows a capillary zonal electrophoresis (CZE) of pseudomycins A, B, C and syringomycin.

STATEMENT OF DEPOSIT

*P. syringae* MSU 16H is publically available from the American Type Culture Collection, Parklawn Drive, Rockville, Md. as Accession No. ATCC 67028. During the pendency of this application, access to the deposit will be forwarded to one determined by the Commissioner to be entitled thereto. All restrictions imposed by the depositor on the availability to the public of the deposited material will be irrevocably removed upon the granting of the patent. The deposit will be maintained for a period of at least thirty years or at least five years after the most recent request for the furnishings of a sample of the deposited material. The deposit will be replaced should it become necessary due to inviability, contamination or loss of capability to function in the manner described in the specification.

DETAILED DESCRIPTION OF THE INVENTION

In accordance with the present invention, *Pseudomonas syringae* MSU 174 was isolated from a Montana barley field. In an attempt to increase antimycotic production, MSU 174 was mutagenized by transposon mutagenesis using TN 905. A "super producer" was isolated and called strain 206. Strain 206 was labeled *P. syringae* MSU 16H and used in the purification of pseudomycin. A culture of *P. syringae* is on deposit at Montana State University and available from the American Type Culture Collection. Other sources of *pseudomonas syringae* known in the art may also be used. *P. syringae* MSU 16H was stored in 15% glycerol at −70° C.

The growth characteristics of *P. syringae* and its antimycotic (toxin) production in the absence of its host are determined. This is preferably assayed with a growth curve, the time of maximum antimycotic toxin production, and possible induction of antimycotic production by compounds from plants or fungi affected by the antimycotic.

Some antimycotic producing plant pathogenic fungi lose their ability to produce their antimycotic in the absence of the host plant or constituents of the host plant. In other cases there may be some constitutive production of the antimycotic, but the amount produced is increased in the presence of plant material. This phenomena has also been observed with some, but not all, strains of *P. syringae.*

In order to determine the most advantageous method for culturing *P. syringae*, the following was performed: Data for a growth curve was gathered for modified Dyes media. Two tubes, each with 3 ml of mDyes was inoculated with a single colony of *P. syringae* MSU 16H then grown in shake culture (180 rpm) at room temperature, overnight. After 24 hours, these cultures contained ≈6×10⁷ org./ml and were used to inoculate two side arm flasks containing 250 ml of mDyes. The bacteria were grown in shake culture, at room temperature, for a total of six days. At timed intervals (0.5, 1, 2, 4, 8, 24, 48, 72, and 96 hours) Klett readings were taken on a Klett-Summerson model 800-3, photoelectric calorimeter. Klett readings were averaged then recorded as Klett units versus time (hours). The instrument was zeroed with uninoculated media.

The same procedure was repeated to obtain a growth curve with potato dextrose in broth (PDB) in still culture.

Figure 7:
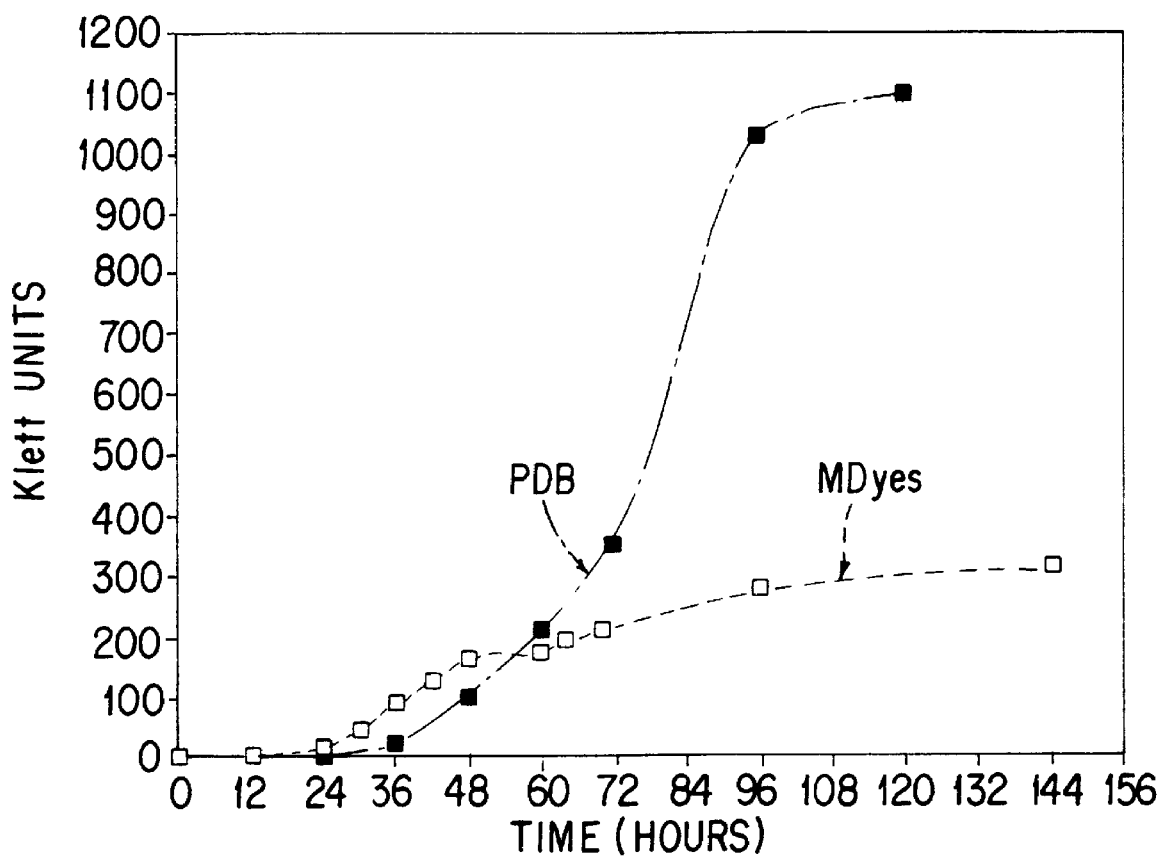

Growth of *P. syringae* MSU 16H followed the "normal" sigmoidal growth pattern when grown in mDyes medium. With reference to FIG. 7, the bacteria remained in lag phase for up to 24 hours at which time they entered logarithmic growth. Growth tapered off and entered stationary phase at about 96 hours. A similar growth pattern resulted with PDB, however, the bacteria reached log phase and stationary phase later, 36 hours and 144 hours respectively (FIG. 7). The PDB culture also reached a higher density than the mDyes culture.

As one of ordinary skill in the art will appreciate, it is sometimes advantageous to use a minimal media when growing cultures for natural product isolation, to minimize extraneous compounds requiring separation from the natural product. A preferred media comprises potato dextrose in broth (PDB). The dyes media may be supplemented with $FeCl_3$, ornithine, and histidine. In a most preferred embodiment, cells are grown in potato dextrose in broth (PDB) as a still culture at 23° C. for 6 days.

*P. syringae* may also be cultured in other media such as Dyes salts with either 1.5% glucose, 0.5% yeast extract (YE), or 2% proteose peptone #3 (PP) wt/v), and/or with the addition of arbutin or geotrichum.

To examine antimycotic production over time, fifteen 100 ml aliquots of PDB, were inoculated with a 3 ml overnight culture of *P. syringae*. The cultures were grown in triplicate as still cultures at room temperature for 0, 3, 6, 9, and 12 days before fractionation by acetone precipitation. Each fraction was dried under nitrogen and weighed. The preparation was resuspended in 50% 1-propanol with 0.1% TFA at concentrations of 500, 50, 5, 0.5 and 0.05 µg/µl. Each of these (10 µl) was spotted onto PDA and bioassayed (Table 1).

The presence of antimycotic was detected as early as 6 days when a total of 500 µg was spotted (10 µl of 50 µl/µl). The activity seemed to remain the same until the termination of the experiment at 12 days. With reference to FIG. 7, the bacterial culture entered the stationary phase of growth at 6 days.

TABLE 1

Production of pseudomycin over time.

| | | concentration (µg/µl) | | | | |
|---|---|---|---|---|---|---|
| Day | Dry Wt. (g/100 ml) | 500 | 50 | 5 | 0.5 | 0.05 |
| 0 | 2.32 +/- .01 | - | - | - | - | - |
| 3 | 1.67 +/- .09 | - | - | - | - | - |
| 6 | 1.36 +/- .47 | + | + | - | - | - |
| 9 | 1.10 +/- .18 | + | + | - | - | - |
| 12 | 1.01 +/- .30 | + | + | - | - | - |

+ = zone of inhibition,
- = no zone of inhibition.

Purification of pseudomycin is challenging due to the potential loss of biological activity at various stages of purification. Conditions such as pH, heat stability, and solvent solubilities must be considered. In addition, there are problems such as ionic exchange or nonspecific irreversible binding to glass, silica, or even column packing material.

Prior art problems with instability were corrected by using compatible solvents and maintaining a low pH by adding TFA to all the solvents.

Acetone precipitation, followed by column chromatography with the nonionic adsorbent, Amberlite XAD-2 column, proved to be a satisfactory method of purification. A typical problem with the separation of peptides by RP-HPLC is exceedingly long retention times. However, according to the present invention, this problem is solved by the addition of the ion pairing agent TFA, and the use of a gradient rather than an isocratic system.

In accordance with the present invention, pseudomycin may be initially purified by either butanol extraction or acetone precipitation. Acetone precipitation is the preferred embodiment.

Butanol Extraction

Cultures are centrifuged, preferably at 5000X g for 10 minutes to pellet the cells. The supernatant liquid is flash evaporated, preferably to 200 ml at 38° C., then extracted about three times with an equal volume of 1-butanol. The butanol fraction may be extracted with water, then the butanol phase flash evaporated to dryness at 38° C. The dried concentrate may be resuspended in methanol for transfer, then dried under nitrogen for storage at –20° C.

Acetone precipitation

Cultures are preferably mixed 1:1 (v/v) with acetone then centrifuged at 5000 X g for 10 minutes. The liquid supernatant is flash evaporated to 200 ml, then brought to a final concentration of 60% acetone. This may be allowed to precipitate overnight at 4° C. with gentle stirring. The precipitate is removed by centrifugation at 5000 X g for 10 minutes. The liquid supernatant is flash evaporated to dryness.

The preferred method of further pseudomycin purification is by eluting the sample through a column. A typical problem with the separation of peptides by RP-HPLC is exceedingly long retention times. However, according to the present invention, this problem is solved by the addition of the ion pairing agent TFA, and the use of a gradient rather than an isocratic system.

Generally, Amberlite XAD-2 (mesh size 20–60) is washed with 0.1% TFA, then packed in a 1.6×40 cm column. The column is equilibrated with 0.1% TFA. The sample prepared by either method above (butanol or acetone procedure) is preferably suspended in one liter 0.1% TFA and loaded onto the column at 1 ml/min with a Waters M25 solvent delivery system. Pseudomycin is preferably eluted with a nonlinear gradient of 1 to 100% 1-propanol with 0.1% TFA and the column eluate monitored at 254 nm. The gradient former is preferably a Kratos Spectroflow 430. Fractions may be collected with a Gilson microfractionator and tested for bioactivity, preferably antifungal activity. Active fractions are pooled, dried with a rotary evaporator, and resuspended in 50% 1-propanol containing 0.1% TFA, and filtered through a 0.2 micrometer Millipore filter.

Final drying of small quantities for analysis before storage at –20° C. may be accomplished by placing the sample under a flow of nitrogen gas. The sample (10 microliters) was applied to a PDA plate and allowed to dry. The plate was oversprayed with a sterile water suspension of *Geotrichum candidum*, sealed with parafilm, and incubated at room temperature. Zones of complete inhibition were noted.

Active fractions from the Amberlite column, after filtering through a 0.2 micron filter (Gelman Sciences) are subjected to reverse phase high performance liquid chromatography (RP-HPLC) on a 4.6×100 mm C8 column (Amicon MC-250) with a 1-propanol, nonlinear gradient (0 to 30% 1-propanol, 0.1% TFA, Waters #2 gradient over 35 minutes). The flow rate of the mobile phase is preferably 1 ml/min. Each peak is collected, evaporated, and resuspended in 50% 1-propanol with 0.1% TFA before being bioassayed. Single active peaks are combined then reinjected for further purification.

Collections from a single peak are preferably again subjected to RP-HPLC utilizing a second solvent system. The samples are eluted with a linear, acetonitrile, 0.1% TFA gradient (Waters #6, 0 to 80% acetonitrile, 0.1% TFA) over a 20 minute period.

Purification of larger quantities of pseudomycin may be performed on a 10×250 mm Amicon MC-250 C8 preparative column with a flow rate of 2 ml/min.

With both columns, a Waters system should be used including a model 440 absorbance detector monitoring at a wavelength of 254, and a model 660 solvent programmer. Two solvent delivery systems are highly preferred, a model M45 and a model A6000.

Collections from each peak to be used for biological testing may be flash evaporated and resuspended in 50% 1-propanol containing 0.1% TFA. Samples for mass spectrometry may be flash evaporated then concentrated, but not dried, under nitrogen. Samples for amino acid analysis may be collected from the HPLC directly into polypropylene cryovials, and assayed directly without further concentration.

FAB Mass Spectrometry

Fast atom bombardment (FAB) mass spectrometry may be performed in order to determine the molecule weight of the pseudomycin. Mass spectrometry utilizing electron bombardment for peptides requires chemical degradation and derivatization, while FAB mass spectrometry makes it possible to analyze underivatized large polar biomolecules.

Analysis is preferably carried out with a VG MassLab Trio2 automated mass spectrometer connected to a Hewlett Packard model 5890 gas chromatograph. The column is preferably a 30 meter P-5 microcolumn. The sample may be run in both a glycerol and thioglycerol matrix.

Nuclear Magnetic Resonance

The proton nuclear magnetic resonance (NMR) spectrum may be recorded on a 500 MHz Bruker spectrometer. Chemical shifts are preferably recorded in ppm units relative to trimethylsilane (0 ppm) with $D_2O$.

Absorbance Characteristics

Pseudomycin, dissolved in 0.1% TFA, may be scanned on a Beckman DU-50 Spectrophotometer. The solution (100 μl) is weighed on a Cahn model G electrobalance to obtain a value for the calculation of the molar concentration. The molar extinction coefficient can be calculated using the maximum absorbance and the molar concentration. The scan and weighing are preferably repeated three times and the average result recorded.

Thin Layer Chromatography

The RP-HPLC sample of pseudomycin (3 μg) may be spotted onto a silica gel 60 P254 thin layer plate (E. Merck Science). The same amount of syringomycin may be spotted adjacent to the pseudomycin for a comparative standard. TLC plates are preferably run in three separate solvent systems; 1) 1-butanol:pyridine:acetic acid:water, 2) 1-butanol:2-picoline:acetic acid:water, and 3) 1-butanol:2,6-lutidine:acetic acid:water. The ratio should be the same for each system, 15:10:3:12, (v/v). TLC plates are then sprayed with ninhydrin reagent; 0.5% ninhydrin in 95% ethanol (v/v). The compounds will appear as light purple spots.

Purity is mandatory for the proper identification of an unknown compound. A single peak upon elution from the HPLC column is suggestive of purity but in itself is not enough. Thin layer chromatography (TLC) is one method for examining purity. Peptides are markedly hydrophilic compounds and are only slightly soluble in nonaqueous solvents. Solvent systems used in their separation must generally contain water.

Capillary Electrophoresis (CE)

This is preferably performed on an Applied Biosystems model 270a instrument. Samples of the antimycotics may be loaded into a 50 μm×72 cm fused silica capillary by vacuum aspiration, then electrophoresed at 25 kV, 24 μA, 38° C., in 50 mM-acid. Peaks are detected at 200 nm. The absorbance of the effluent should be monitored at 254 nm.

Amino Acid Analysis

For the amino acid analysis, a model 420 derivatizer coupled to a model 130 HPLC system is preferably utilized. Data may be acquired and analyzed by a model 920 software system. Amino acid sequencing may be performed with a model 477 sequencer with one line PTH amino phenylthiohydantoin (PTH) amino acid analysis. Peak quantitation may be performed by software supplied with the model 477 sequencer. Further, peak identification may be performed manually by comparison to standard chromatograms.

Heat Stability

The heat stability of the pseudomycin may be analyzed according to the following method: A 1-butanol crude extract (75 μl) of pseudomycin, at a concentration of 33 μg/μl, are preferably placed into each of eight 1.5 ml Eppendorf tubes (or reactivials for the 100° C. test). Tubes are then incubated preferably at each of four separate temperatures (e.g. 15°, 30°, 60°, and 100° C.) for a period of time, preferably six days. Samples (5 μl) may be removed from each tube at 0, 0.5, 1, 2, 4, 8, 24, 48, 72, and 96 hours and spotted on a PDA plate. After drying, the plates are oversprayed with *G. candidum*, then incubated at room temperature overnight. Inhibition was recorded as plus or minus at each time and temperature.

pH Sensitivity

The pH sensitivity of the pseudomycin may be analyzed according to the following method: a 1-butanol crude extract (5 μl), at a concentration of 100 mg/ml, is dissolved in 200 μl of the treatment solution (Table 2). The concentration of each buffer may be 0.01M. Each buffer is adjusted to a pH equal to its $pK_a$ with 1M sodium hydroxide or 1M hydrochloric acid. The samples are incubated at room temperature for a period of time, preferably four days. At 0, 1, 2, 3, and 4 days, each solution (10 μl is spotted onto PDA and bioassayed. All treatments may be run in duplicate. The positive control is the 1-butanol extract dissolved in water and methanol. The negative controls are the buffers without the extract.

TABLE 2

Buffers for testing pH sensitivity of the antimycotic.

| Buffers | pH |
| --- | --- |
| 1. Citric Acid | 3.06 |
| 2. Citric Acid | 4.75 |
| 3. Ammonium Acetate | 4.75 |
| 4. Citric Acid | 5.40 |
| 5. Pipes | 6.80 |
| 6. Tris | 8.00 |
| 7. Tris | 9.00 |
| 8. Boric Acid | 10.00 |

The stability of the pseudomycin in various solvents may be analyzed according to the following method: A 1-butanol crude extract (5 μl at 33 μg/μl) is added to 100 μl of solvent. Each solvent (100 μl) alone is used for the negative control. The solutions are incubated at room temperature for 24 hours, at which time they are dried under nitrogen then resuspended in 15 μl of methanol and 10 μl are removed for bioassay.

The solvents tested may be: 1-propanol, (50% and 100%); TFA, (1, 2, and 3M); HCL, (0.5, 1, 2, and 4M); 0.1% TFA, 10% acetonitrile; 0.1% TFA, 90% acetonitrile; 100% 1-butanol; 100% methanol; 100% water; and 0.1% TFA.

Before a protocol for antimycotic purification can be adopted, a good bioassay must be developed which is preferably both sensitive and quantitative. The overspray method utilizing *G. candidum* is the method of choice because of the availability of the organism. Fractions resulting from the various purification steps are spotted onto PDA and allowed to dry. The plate is oversprayed with a sterile water suspension of the fungus then incubated overnight at room temperature. Presence of antimycotic is indicated by a clear zone of inhibition. Weak zones of inhibition, that eventually overgrew with mycelia, are considered negative.

Known amounts of crude extract are spotted for assay on separate PDA plates. Great variation of zone size is noted depending on the age of the plate and the amount the solution spread on the plate. To reduce variation, the samples are preferably applied to antibiotic filter discs which are then laid on the agar plate before overspraying. The antimycotic adsorbed to the disc, preventing diffusion onto the agar plate. Results in the bioassays are recorded as plus or minus.

With regard to the purification of pseudomycin, solvents used during the purification procedures could affect the activity of the antimycotic. In accordance with the present invention, 165 μg of 1-butanol crude extract was added to 10 μl of the solvent to be tested. Each vial was incubated for 24 hours at room temperature then dried under nitrogen and resuspended in 15 μl of methanol. An aliquot (10 μl) was removed from each vial and bioassayed. Each solvent was tested without the crude extract as a negative control. Pseudomycin remained active in all solvents tested except the 4M HCl (Table 3). TFA at 3M, and the remaining concentrations of HCl, also decreased the zones of inhibition.

TABLE 3

Sensitivity of toxin to different solvents.

| Solvent | Treatment | Control |
|---|---|---|
| 100% 1-propanol | ++ | − |
| 50% 1-propanol | ++ | − |
| 3 M TFA | + | − |
| 2 M TFA | ++ | − |
| 1 M TFA | ++ | − |
| 0.5 M TFA | ++ | − |
| 0.1% TFA, 10% acetonitrile | ++ | − |
| 0.1% TFA, 90% acetonitrile | ++ | − |
| 0.5 M HCl | + | − |
| 1 M HCl | + | − |
| 2 M HCl | + | − |
| 4 M HCl | − | − |
| 100% 1-butanol | ++ | − |
| 100% methanol | ++ | − |
| 100% water | ++ | − |
| 100% water, 0.1% TFA | ++ | − |

− = no zone of inhibition
+ = a zone of inhibition < 1 cm. dia.
++ = a zone of inhibition > or = 1 cm. dia.

Other solvents may be tested in a similar manner.

Cells were grown for six days in still culture in PDB at room temperature. The culture was mixed 1:1 (v/v) with acetone then centrifuged to remove cellular debris. The supernatant was first flash evaporated to 200 ml, then acetone was added to 60% (v/v). The mixture was allowed to precipitate overnight. Precipitate was removed by centrifugation. Antimycotic activity remained in the supernatant liquid.

Figure 8A:
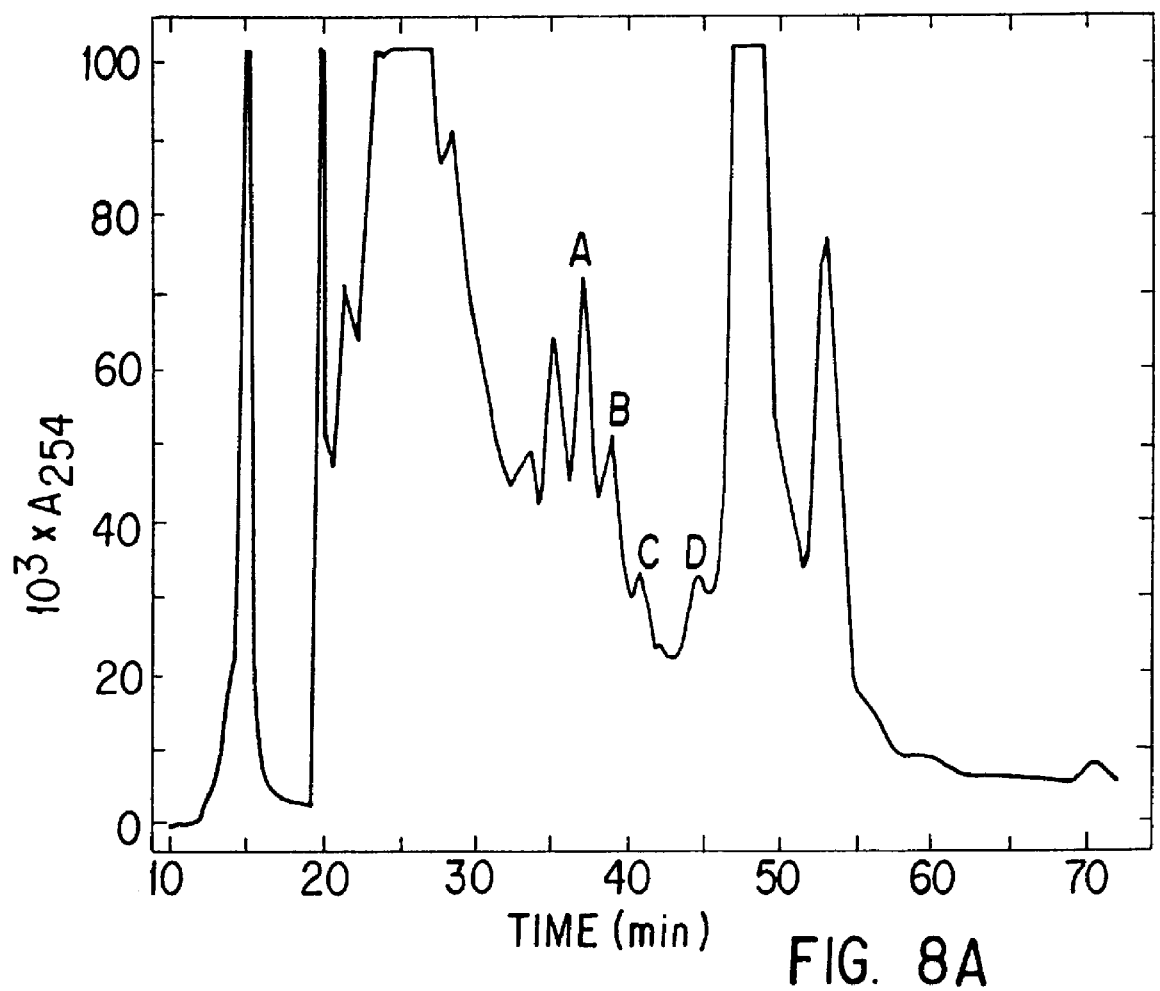
Figure 8B:
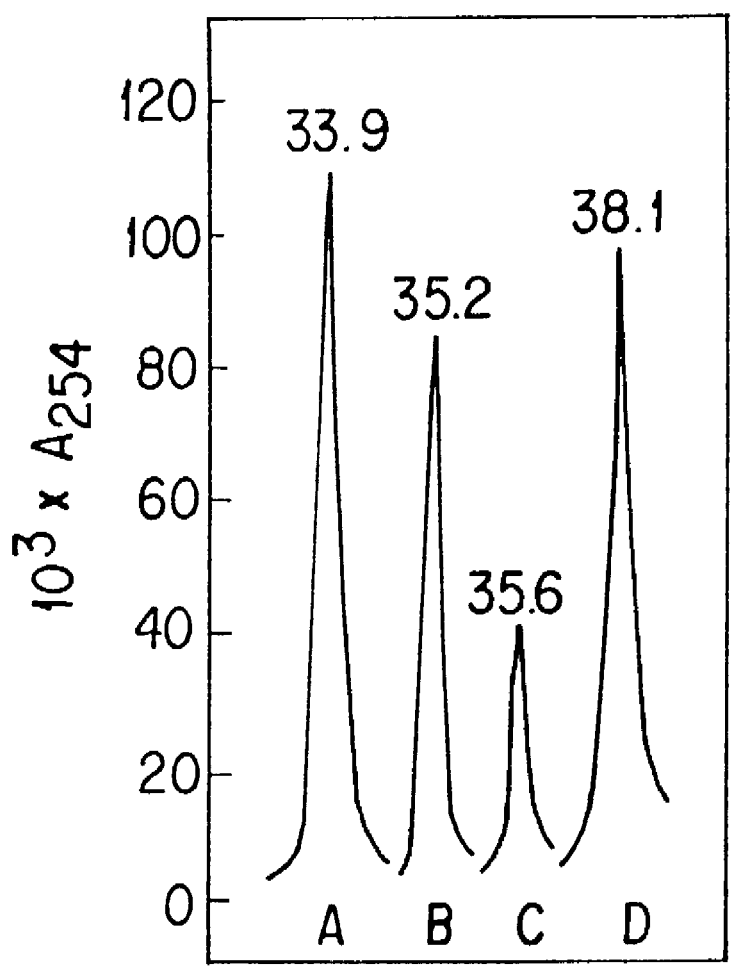

The supernatant liquid of the PDB media was concentrated, then resuspended in one liter of 0.1% trifluoroacetic acid (TFA), and loaded onto an Amberlite XAD-2 column. After elution with a propanol gradient, the fractions were bioassayed. With reference to FIG. 8, the pseudomycin fraction from Amberlite XAD-2 chromatography was resolved into its four components by reversed-phase HPLC using a C-8 column and a hyperbolic gradient of 10 propanol in TFA. Letters refer to the respective pseudomycins, A–D. Each pseudomycin fraction was then rechromatographed on the same column, but was eluted with a linear gradient of acetonitrile in TFA. A composite chromatograph of the four single peaks, and the retention times (min), observed in these second runs is presented in the inset.

Positive fractions were combined, filtered, and subjected to reverse phase high performance liquid chromatography (RP-HPLC). Two different solvent systems were utilized; 1) a 1-propanol nonlinear gradient, and 2) an acetonitrile linear gradient. Propanol was the solvent of choice for the separation of peptides and proteins because the concentrations needed for elution are lower than with other organic modifiers, reducing the chance of activity loss. Acetonitrile is a good choice for the same reasons. TFA (0.5%) is necessary for adjustment of the pH and acts as an ion pairing agent. TFA modifies the polarity of the peptide through ion-pair formation which leads to an increase in retention time and therefore, better separation. Volatility of TFA is also a positive aspect when considering amino acid analysis and sequencing.

The propanol gradient was a nonlinear (Waters #2) gradient of 0 to 30% 1-propanol, 0.1% TFA over 35 minutes. Each peak from the propanol gradient was collected, concentrated by flash evaporation, then tested for bioactivity. With reference to FIG. 1, peaks 3, 4, and 6 were found to be active. The eluate collected from 16 to 20 minutes (labeled #5 in FIG. 1) was also active but no definite peak was seen on the elution profile. The retention times are listed in Table 4. These peaks were reinjected for further purification.

TABLE 4

Retention times of peaks from the HPLC after elution with a nonlinear propanol gradient.

| Peak number | retention time |
|---|---|
| 3 | 13 min. 30 sec. |
| 4 | 14 min. 45 sec. |
| 5 | — |
| 6 | 22 min. 0 sec. |

Figure 2:
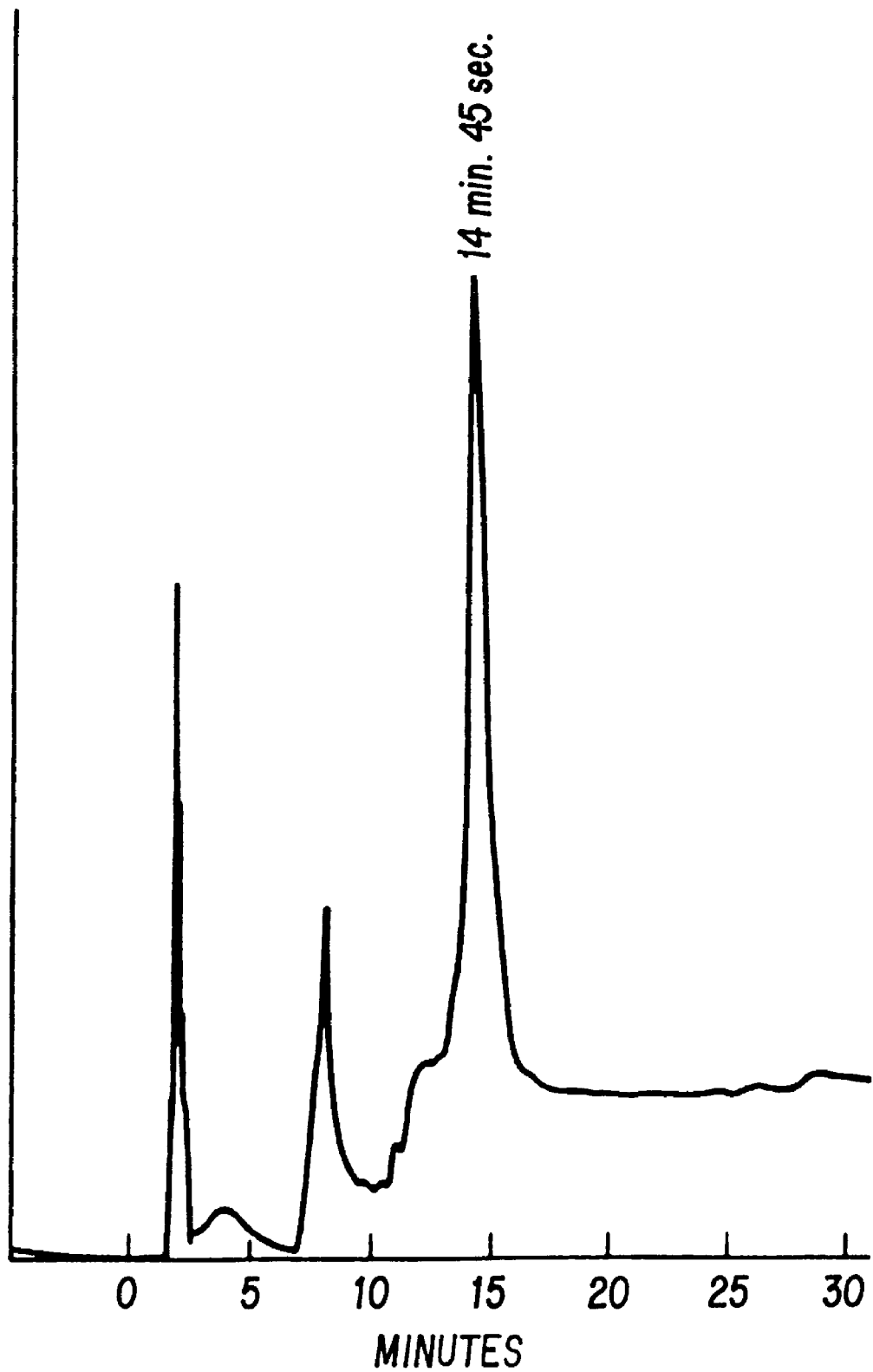

The final step was to subject the eluate from peak #4 to the RP-HPLC with the linear acetonitrile gradient, 0 to 80% acetonitrile over 20 minutes. The retention time was 14 minutes and 45 seconds (FIG. 2). This procedure yielded an average of 0.0015 grams of purified toxin as compared to 0.0002 grams with the butanol procedures. Both the 1-butanol extraction method and the acetone precipitation method resulted in the isolation of the same compound as confirmed by thin layer chromatography and mass spectrometry data.

TABLE 5

Purification table for the acetone precipitation procedure

| Stage of Purification | Grams of Dry Weight per liter | Purification Fold |
|---|---|---|
| PDA culture | 27.6 | 1 |
| 1st acetone ppt. | 15.0 | 1.8 |
| 2nd acetone ppt. | 12.8 | 2.2 |
| Amberlite XAD-2 | 0.016 | 1,725 |
| RP-HPLC | 0.0015 | 18,400 |

As a preliminary check, the eluate collected at the time of each peak from the propanol gradient, was subjected to FAB mass spectrometry. HPLC peak number 4 was the only peak that appeared to be pure, having a single mass ion peak. Mass spectra data from 3 and 5 had more than one peak, one of which had the same mass ion assignment as the peak from HPLC peak number 45. Spectral data for HPLC peak number 6 also showed several peaks but none at the same mass as HPLC peak number 4. It is believed that this may suggest a second antimycotic compound in these preparations.

PDB alone was carried through the same purification steps as the *P. syringae* culture. There were no detectable antimycotics present in PDB alone.

Confirmation of Purity—Thin Layer Chromatography

Figure 3:
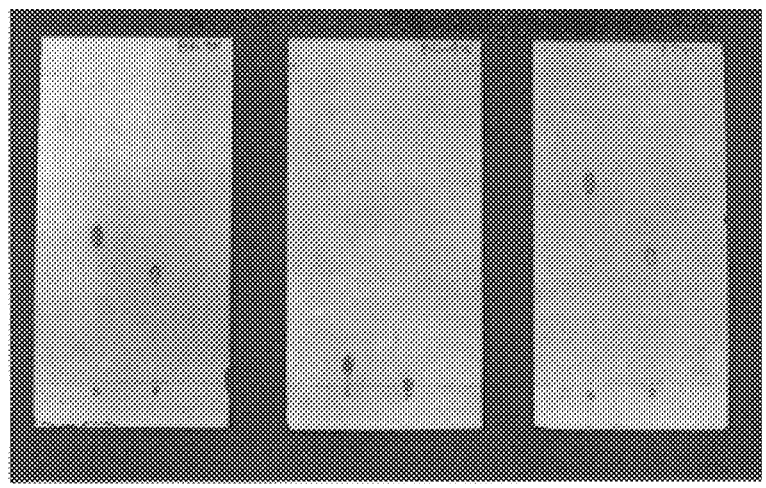

Butanol:pyridine:acetic acid:water (15:10:3:12) was the solvent of choice. The RP-HPLC sample (3 μg) was spotted on to a silica gel TLC plate. Syringomycin was also spotted on the plate for a comparative standard. Both compounds migrated as single spots with $R_f$'s of 0.59 and 0.37, respectively (FIG. 3). Not only did pseudomycin appear pure, but it migrated differently than syringomycin. To further establish purity, pseudomycin was run in two additional solvent systems; picoline or lutidine was substituted for pyridine. These solvents are methylated analogs of pyridine. Again single spots were apparent with $R_f$ values as indicated in FIG. 3.

Chemical Characterization

Figure 4:
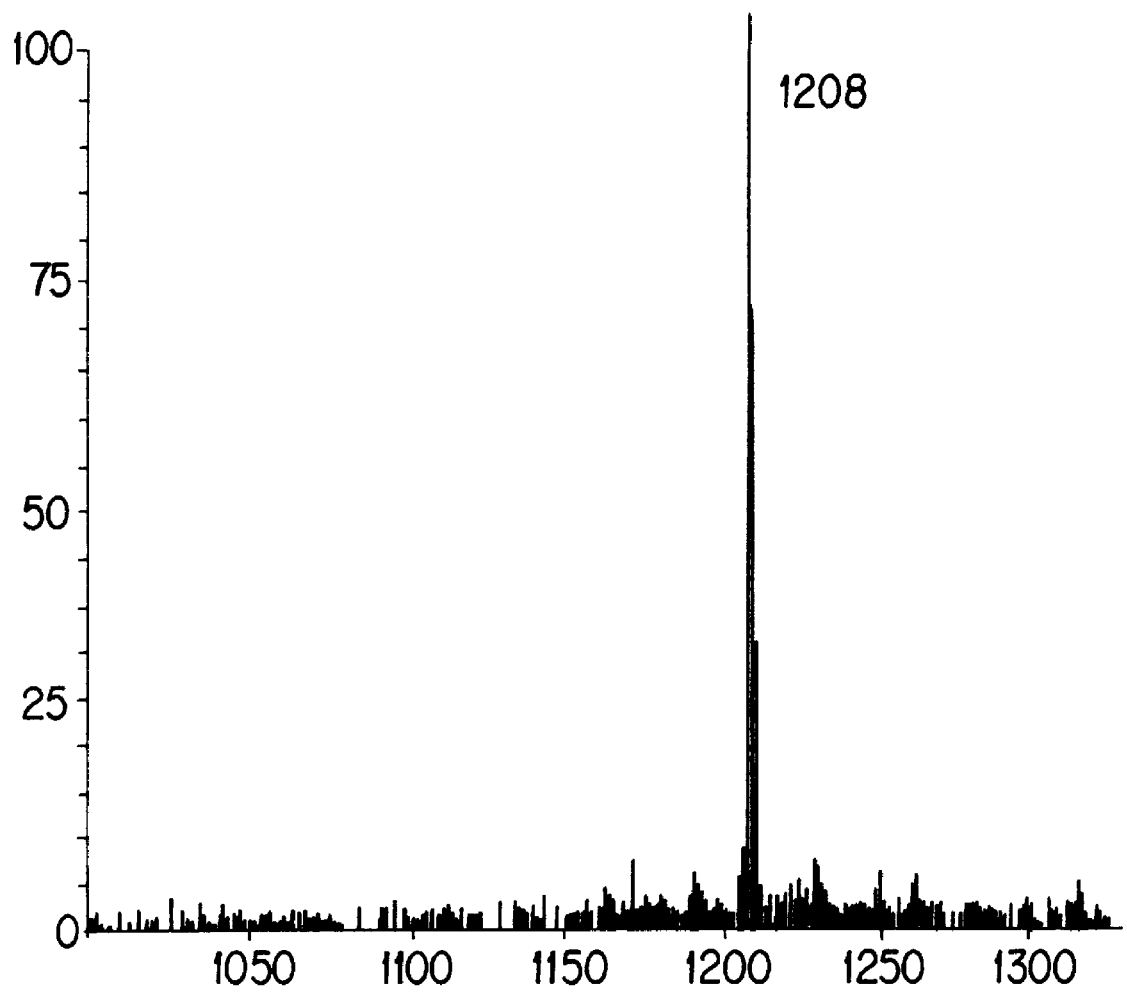

The purified sample was subjected to Fast Atom Bombardment (FAB) mass spectrometry. The sample was run in two different matrices, glycerol and thioglycerol. The mass H+ was found to be 1208 (FIG. 4). The same sample was used for amino acid analysis and sequencing. Preliminary results for pseudomycin indicate the presence of seven amino acids; aspartate, serine, lysine, phenylalanine, and arginine (1:1:1:3:1) and one unknown amino acid. The amino acid analysis of syringomycin is arginine, phenylalanine, serine, and 2,4-diaminobutyric acid (1:1:2:2).

Figure 5:
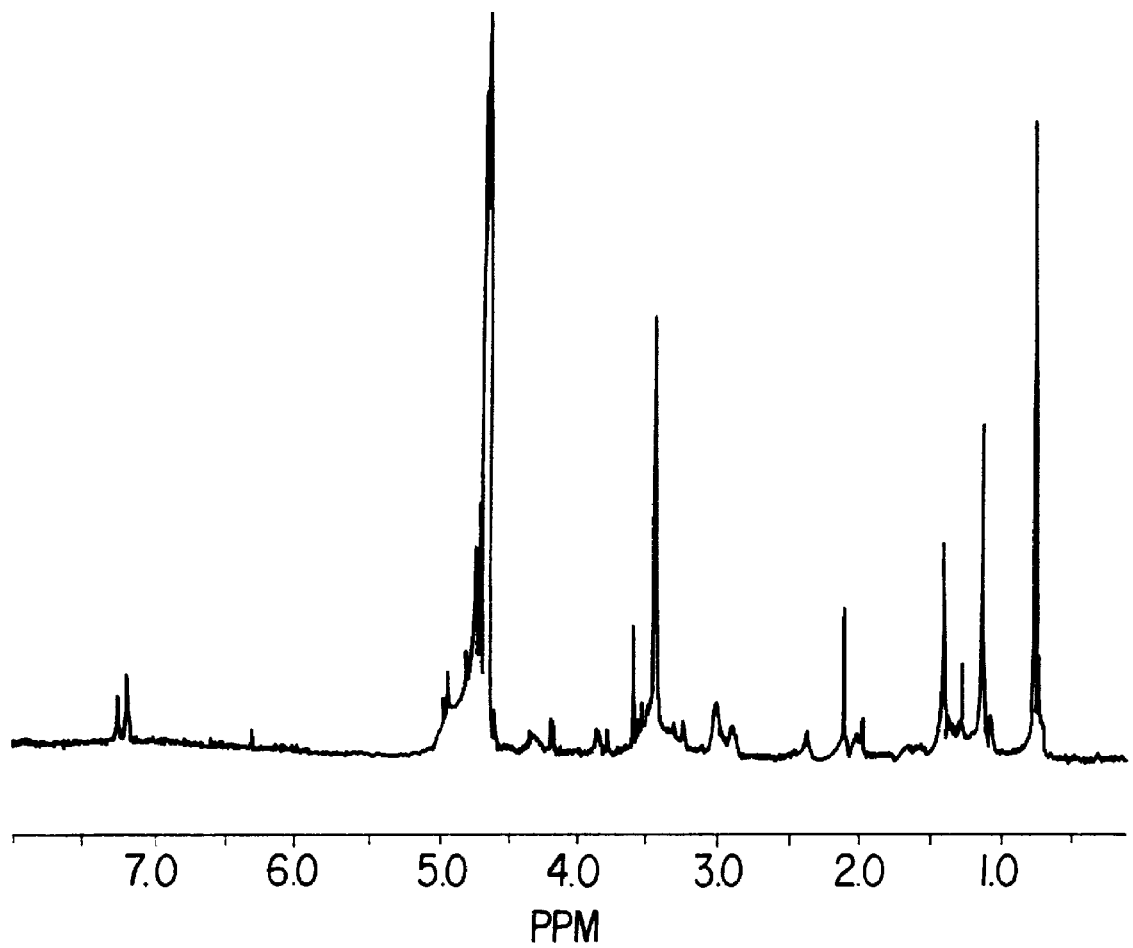

Using post column derivatization, with the Applied Biosystems instrumentation, the fourth amino acid in syringomycin, 2,2-diaminobutyric acid, is undistinguishable from phenylalanine. The $^1$H-NMR spectrum (FIG. 5) indicates the presence of protons on an aromatic ring in the range of 7.1–7.4 ppm which may be from phenylalanine. This suggests that phenylalanine is one of the amino acids but does not rule out the presence of 2,3-diaminobutyric acid. The sum of the molecular weights of the suspected amino acids is considerably lower than the mass contained from the FAB mass spectrometry data. This may be due to the presence of a long chain fatty acid attached to the peptide, similar to the one found in syringomycin.

Figure 6:
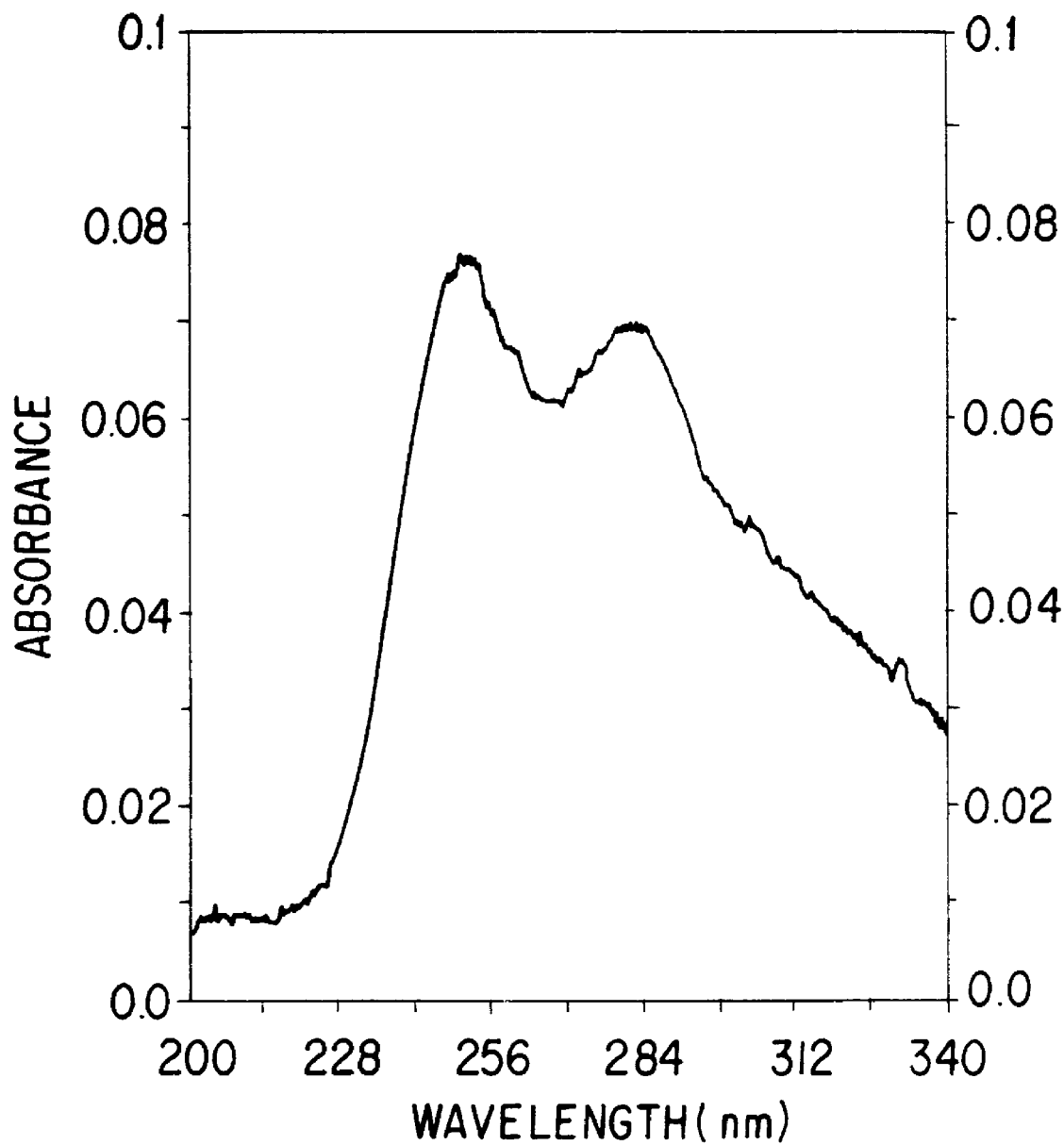

Pseudomycin, dissolved in 0.1% TFA, was scanned using a spectrophotometer. There were two peaks of absorbance (FIG. 6); one at 254 nm and one at 280 nm. The solution (100 μl) was weighed on an electrobalance. The molar extinction coefficient was calculated for each wavelength; $Am_{254}=167$, $Am_{280}=146$.

Heat stability was tested at four different temperatures; 15°, 30°, 60°, and 100° C. (Table 6). Butanol crude extract (75 μl) of pseudomycins, at a concentration of 33 μg/μl placed into each of eight 1.5 ml Eppendorf tubes. Tubes were then incubated at each of four temperatures (15°, 30°, 60° and 100° C.) for six days. Throughout the incubation period, samples (5 μl) were removed from each tube at 0, 0.5, 1, 2, 4, 8, 24, 48, 72 and 96 h and spotted on a PDA plate. After drying, the plates were oversprayed with *G. candidium* ($10^6$ cells ml$^{-1}$), then incubated at room temperature overnight. Zones of growth inhibition were recorded as ++(>2 cmJ), +(<2 cm), or −(no inhibition). The experiment was repeated twice with identical results. There was total loss of activity by the fourth day. When the extract was incubated at 100° C. there was a large decrease in the zone of inhibition for antimycotic heated 30 minutes and a complete loss of activity for antimycotic heated four hours. This antimycotic demonstrates considerable heat stability.

TABLE 6

Heat stability of the toxin.

| Temp. °C. | Time (hours) | | | | | | | | | |
|---|---|---|---|---|---|---|---|---|---|---|
| | 0 | 0.5 | 1 | 2 | 4 | 8 | 24 | 48 | 72 | 96 |
| 15 | ++ | + | ++ | ++ | + | + | ++ | + | + | + |
| 30 | ++ | ++ | ++ | ++ | ++ | + | ++ | + | + | + |
| 60 | + | + | + | + | + | + | + | + | + | + |
| 100 | ++ | + | + | + | − | − | − | − | − | − |

+ = zones of inhibition < 2 cm.
++ = zones of inhibition > or = 2 cm.
− = no apparent zone of inhibition.

Partially purified pseudomycin (5 μl), at a concentration of 100 mg/ml, was dissolved in 200 μl of water, methanol (positive control), and each of eight different buffers (0.01M). In addition, one tube of each treatment without the extract was prepared as a negative control. Each buffer was adjusted to a pH equal to its $pK_a$. Each solution was incubated at room temperature. After 0, 1, and 2 days, 10 μl of each solution was spotted onto PDA and bioassayed. Pseudomycin remained active in the water, methanol, and the buffers at or below a pH of 4.75 (Table 7). Activity in buffers at or above pH 5.4 was apparent initially but the zones of inhibition were overgrown in two days. The static inhibition was also noted in the same control treatments and may be due to high pH values. These were recorded as negative results.

TABLE 7

Sensitivity of activity to pH changes.

| Treatments | pH |
|---|---|
| 1. Citric Acid | 3.06 |
| 2. Citric Acid | 4.75 |
| 3. Ammonium Acetate | 4.75 |
| 4. Citric Acid | 5.40 |
| 5. Pipes | 6.80 |
| 6. Tris | 8.00 |
| 7. Tris | 9.00 |
| 8. Boric Acid | 10.00 |

| | Results | | | | | | | |
|---|---|---|---|---|---|---|---|---|
| Day | 1 | 2 | 3 | 4 | 5 | 6 | 7 | 8 |
| 0 | + | + | + | + | + | + | + | + |
| 1 | + | + | + | + | + | − | − | − |
| 2 | + | + | + | + | + | − | − | − |
| 3 | + | + | + | + | + | − | − | − |
| 4 | + | + | + | + | + | − | − | − |

Table 8 below summarizes the effects of solvent and pH on the antimycotic activity of pseudomycins.

TABLE 8

Effects of solvent and pH on the antimycotic activity of the pseudomycins

| Solvent | Antimycotic activity* | Buffer | Inhibition† |
|---|---|---|---|
| 100% 1-butanol | ++ | Citrate, pH 3.1 | + |
| 50% 1-propanol | ++ | Citrate, pH 4.8 | + |
| 100% 1-propanol | ++ | Acetate pH 5.4 | − |
| 100% methanol | ++ | PIPES, pH 6.8 | − |
| 100% water | ++ | Tris, pH 8.0 | − |
| 0.1% TFA | ++ | Borate, pH 9.0 | − |
| 10% $CH_3CN$ in 0.1% TFA | ++ | Borate, pH 10.0 | − |
| 90% $CH_3CN$ in 0.1% TFA | ++ | | |
| 0.5 M-TFA | ++ | | |
| 1 M-TFA | ++ | | |
| 2 M-TFA | ++ | | |
| 3 M-TFA | + | | |
| 0.5 M-HCl | + | | |
| 1 M-HCl | + | | |
| 2 M-HCl | + | | |
| 4 M-HCl | − | | |

*A 1-butanol extract of pseudomycins (5 μl at 33 μg μl$^{-1}$) was added to 100 μl of each solvent. Each solvent (100 μl) was used as a negative control. The solutions were incubated at 23° C. for 24 h, then dried under $N_2$ and resuspended in 15 μl methanol. Each methanol extract (10 μl) was then spotted on a PDA plate, after which the plate was dried, oversprayed with G. candidum (10$^6$ cells ml$^{-1}$), and incubated at room temperature overnight. Zones of growth inhibition were recorded as ++ (>2 cm), + (≦2 cm), or − (no inhibition). No inhibition of fungal growth was observed with any of the controls (data not shown).
†Duplicate 5 μl aliquots of a l-butanol extract of pseudomycin (100 μg μl$^{-1}$) were dissolved in 200 μl of 10 mM-buffer. After incubation for 48 h at room temperature, a 10 μl aliquot was bioassayed as described above. Zones of growth inhibition were recorded as + (≦2 cm) or − (no inhibition). Positive controls, using methanol instead of buffers, showed clear zones of inhibition. Negative controls, using buffers alone, showed no inhibition. The experiment was repeated twice with essentially the same results.

Purity of Pseudomycins

Capillary electrophoresis (CE) and TLC were used in addition to HPLC to assess the purity of the pseudomycin preparations. In addition, since other strains of P. syringae produce syringomycin, an antimycotic with chromatographic properties similar to those of the pseudomycins, CE and TLC was used to determine whether syringomycin was identical to one of the pseudomycins.

Figure 9:
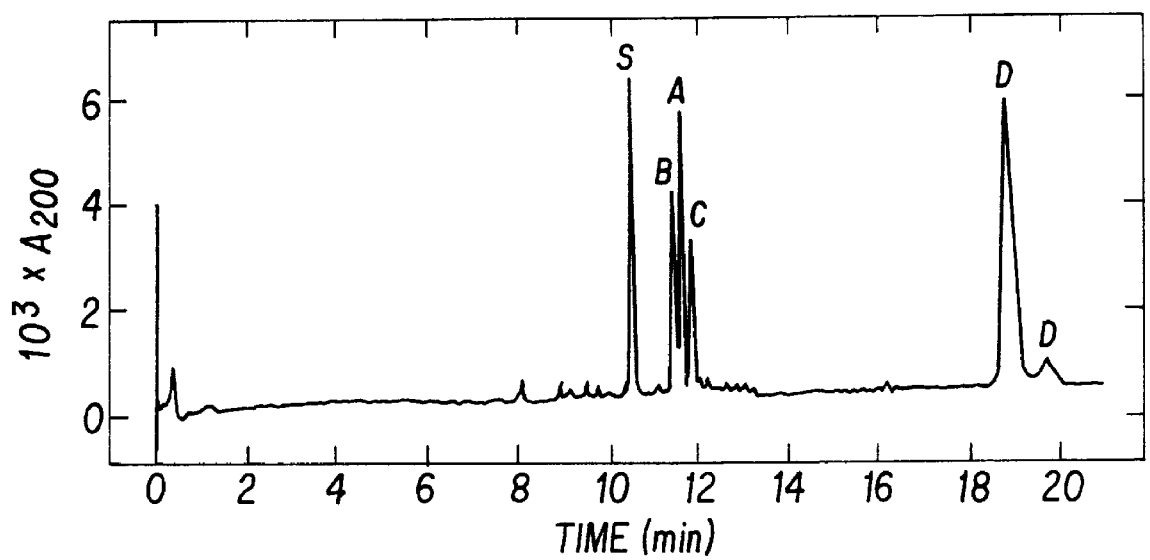

Pseudomycins A, B, and C each produced a single, sharp, major peak in CE; these peaks represented 95% 94%, and 95% respectively, of the total UV-absorbing material present in each fraction. Syringomycin also displayed a single, predominant peak, containing 83% of the total UV-absorbing material in the preparation. All five samples were then electrophoresed together to determine if any co-migrated. All had unique electrophoretic mobilities (FIG. 9). Thus each of the pseudomycins of the invention has a purity of about 95%.

With regard to FIG. 9, approximately 3 ml each of syringomycin and pseudomycins A–C were loaded into the capillary. Electrophoresis was performed as specified previously. The abscissa represents electrophoretic migration time, measured from the anodic end of the capillary to the detector. Peaks are denoted as follows: S. syringomycin; A, B and C, pseudomycins A, B, and C and a minor component found with D, respectively.

To ensure that loading order did not affect migration times, the pairs of pseudomycins A plus B and A plus C were re-electrophoresed after loading in both possible orders. The relative electrophoretic mobilities for the three samples remained constant. The mobility differences of syringomycin and D relative to the triplet of A, B and C are so large that loading order would not affect their relative positions.

TLC experiments yielded analogous results. Each of the pseudomycins and syringomycin migrated as a single spot with a unique $R_f$ value in each of the different TLC systems. In all cases, syringomycin migrated with a higher $R_f$ than did the pseudomycins.

Amino Acid Analysis

Amino acid compositions were determined using an Applied Biosystems model 420A/130A derivatizer-analyzer. Briefly, approximately 200–900 pmol of each sample mixed with Inmol L-norleucine, was dried in vacuo in separate 6×50 mm glass tubes. These tubes were then sealed, in vacuo, inside 18×150 mm Pyrex culture tubes containing 300 μl 6M-hydrochloric acid (Pierce Chemical Co.). Gas-phase hydrolysis was performed by heating at 170° C. for 30–45 minutes. After cooling, each sample tube was removed from the ignition tube and dried in a Speed-Vac concentrator (Savant).

Hydrolysis products were dissolved in 15 μl 0.025% (w/v) $K_3$H-ethylenediaminetetra-acetate (EDTA) and spotted onto the glass reaction slides of the model 420A/130A instrument. Phenylthiocarbamoylation and reverse-phase HPLC were performed automatically by the 420A/130A instrument, essentially according to the manufacturer's instructions. "Dab" refers both to Phe and Dab (diaminobutyric acid), since these molecules co-elute from the HPLC. "Dab" peaks were collected and dried down prior to CE. Moles of each amino acid were first determined using molar absorptivity values derived from hydrolysed amino acid standards, then were normalized using the internal standard L-norleucine. 3-Hydroxyaspartic acid eluted in a region containing an injection artifact, prior to any of the other amino acids.

Protein Sequence Analysis

Sequencing was done on polybrene-coated glass fibre supports using an Applied Biosystems model 477A/120A pulsed liquid sequenator, essentially as suggested by the manufacturer. Phenylthiohydantoin amino acid analysis was performed on-line and sequence assignments were made by visual inspection of chromatograms.

Plasma Desorption Mass Spectrometry (PDMS)

Spectra were acquired using a BioIon 20 instrument (BIO-ION Nordic; now a division of Applied Biosystems), according to the manufacturer's instructions. Samples were dissolved in 0.1% TFA/50% ethanol (in water), dried on nitrocellulose-coated aluminized mylar supports, washed briefly with water, then analyzed. Alkaline hydrolyses were done by incubating 2–5 μl (about 0.1–1 nmol) of sample (from the acetonitrile/C-8 HPLC step) with 20 μl 1% (v/v) ammonium hydroxide (in water) containing either 50% (v/v) ethanol or 50'5 (v/v) n-propanol, for 20 minutes at 22° C. The samples were then dried in a Speed-Vac concentrator, dissolved in 0.1% TFA/alcohol (the same alcohol as was used for hydrolysis), and prepared for PDMS as described above. See Table 9.

TABLE 9

Mass spectral analysis of pseudomycins
The pseudomycins (Pseudo. A–D) and syringomycin were analysed by PDMS, as described in Methods. Masses are those of the most predominant (M + H)$^+$ ions. Samples were run both without being hydrolysed and after alkaline hydrolysis in either ethanol or l-propanol.

| Treatment | Pseudo. A | Pseudo. B | Pseudo. C | Pseudo. D | Syringomycin |
|---|---|---|---|---|---|
| None | 1224.7 | 1208.6 | 1252.6 | 2401.0 | 1226.6 |
| $NH_3 + C_2H_5OH$ | 1270.4 | 1253.3 | 1296.9 | 2384.5 | 1272.0 |
|  | 1243.5 | 1226.1 | 1270.1 |  | 1243.3 |
| $NH_3 + C_3H_7OH$ | 1284.7 | 1264.3 | 1311.7 | 2384.9 | 1284.1 |
|  | 1242.2 | 1226.6 | 1269.8 |  | 1243.0 |

After treatment, pseudomycins A, B and C, as well as syringomycin, produced (M+H)+ ions shifted higher in mass by approximately 17–19 Da, equivalent to one molecule of ammonia or water. A second family of ions was also observed, in which masses were heavier by approximately 44–46 Da, equivalent to one molecule of ethanol (46 Da). These data are consistent with a process in which the lactone is opened to an acid, amide or ester form. Additional evidence for this was obtained when 1-propanol, instead of ethanol, was used in the solvent for hydrolysis and dissolution. In this case, a different high-mass family was observed approximately 60 Da larger than that seen with the untreated molecules (Table 9). This increase is equivalent to the mass of 1-propanol. Pseudomycin D, on the other hand, lost approximately 16 Da following both base treatments. This difference may represent loss of oxygen (16 Da), or substitution of hydroxide for chloride (17 Da) as may occur, for example, at alkaline pH with chlorothreonine. The behavior of pseudomycin D, which is inconsistent with its being a lactone, alone with its molecular mass, distinguish it from other pseudomycins.

Ions with masses corresponding to those of the native molecules, of dehydrated molecules, of dimeric molecules, and of unidentified molecules were also observed but at significantly lower levels than those of the +18, +46 and +60 Da families.

Amino Acid Composition of Pseudomycins

Amino acid analysis were performed on the pseudomycins and syringomycin as described above. Pseudomycins A, B and C had almost identical compositions, containing Asx, Ser, Arg, "Dab" and Lys in the integer molar ratios 1:1:1:3:1, respectively (Tables 10 and 20). The unusual amino acid 3-hydroxyaspartic acid was also detected in each of the three molecules. Syringomycin contained Ser, Arg and "Dab", in the integer molar ratios of 2:1:3, as well as 3(OH)Asp. Significant amounts of aspartic acid or theonine were not detected in syringomycin. The composition of pseudomycin D was more complex. Like the other pseudomycins and syringomycin, it contained Ser, Arg and "Dab". However, unlike the other pseudomycins, it did not have any Asx or Lys, but did have the additional amino acids Gly, Ala, Pro, Tyr, Val and Leu. The results are summarized in Table 10.

Figure 10:
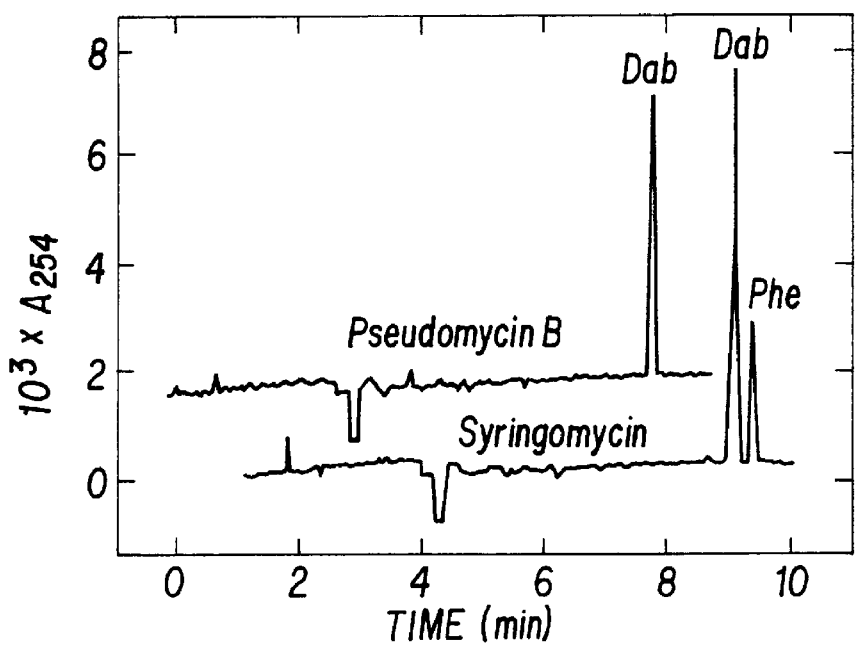

Although not resolved by reverse-phase HPLC, Phe and Dab are baseline-resolved by CE and can be quantified through their UV-absorption. The "Dab" peaks from the amino acid analyzer were thus collected and analyzed in this way. Electropherograms of "Dab" from pseudomycins A–D were essentially identical. Electropherograms from pseudomycin B and from syringomycin are presented in FIG. 10. The "Dab" peak from pseudomycin B was composed entirely of Dab, whereas the "Dab" peak from syringomycin, as expected, contained Dab and Phe in a molar ratio of 2:1.

Pseudomycins A–C have amino acid compositions clearly different from that of syringomycin (Table 10). They have one fewer Ser and contain one each of Asx and Lys, residues which are not detected in syringomycin. In addition, these pseudomycins contain three residues of Dab, whereas syringomycin contains two of Dab and one of Phe.

Syringostatin A may be related to these pseudomycins but is structurally unique, containing Ser, Thr, Dehydro-Thr, Dab, 3-hydroxyaspartic acid, chlorothreonine, homoserine, ornithine and a $C_{14}$ fatty acid. Syringotoxin, another pseudomonad antimycotic, has the same composition as syringostatin A except that it contains one Dab residue and one Gly residue. The composition of pseudomycin D is clearly different from those of any of the other compounds.

TABLE 10

Amino acid composition of pseudomycins

| Amino acid | Molar percentage* | | | | |
|---|---|---|---|---|---|
| | Pseudo. A | Pseudo. B | Pseudo. C | Pseudo. D | Syringomycin |
| 3(OH)Asp† | + | + | + | − | + |
| Asx | 14.1 (1) | 14.7 (1) | 16.0 (1) | 0.7 (0) | 1.2 (0) |
| Glx | 2.1 (0) | 2.9 (0) | 1.1 (0) | 0.9 (0) | 0.6 (0) |
| Ser | 14.6 (1) | 15.9 (1) | 15.5 (1) | 6.4 (2) | 24.4 (2) |
| Gly | 3.1 (0) | 1.9 (0) | 1.4 (0) | 3.6 (1) | 0.8 (0) |
| His | 2.4 (0) | 2.5 (0) | 3.5 (0) | 0.0 (0) | 2.0 (0) |
| Arg | 10.6 (1) | 10.2 (1) | 12.0 (1) | 3.8 (1) | 13.4 (1) |
| Thr | 1.2 (0) | 0.8 (0) | 0.3 (0) | 0.7 (0) | 0.5 (0) |
| Ala | 1.2 (0) | 1.6 (0) | 0.7 (0) | 36.3 (10) | 1.3 (0) |
| Pro | 0.5 (0) | 0.0 (0) | 0.0 (0) | 4.4 (1) | 0.4 (0) |
| Tyr | 0.0 (0) | 0.0 (0) | 0.2 (0) | 3.6 (1) | 0.0 (0) |
| Val | 0.2 (0) | 0.5 (0) | 0.0 (0) | 18.1 (5) | 0.9 (0) |
| Met | 0.8 (0) | 0.0 (0) | 0.9 (0) | 0.0 (0) | 0.0 (0) |
| Cys | 0.0 (0) | 0.0 (0) | 0.0 (0) | 0.7 (0) | 0.0 (0) |
| Ile | 0.2 (0) | 0.0 (0) | 0.7 (0) | 0.1 (0) | 0.2 (0) |
| Leu | 0.0 (0) | 0.0 (0) | 0.0 (0) | 5.1 (2) | 0.6 (0) |
| Dab | 38.2 (3) | 37.9 (3) | 36.5 (3) | 15.3 (5) | 39.2 (3) |
| Lys | 11.0 (1) | 11.1 (1) | 11.1 (1) | 0.3 (0) | 0.2 (0) |

* Samples were hydrolysed, derivatized and analysed as described in Methods: molar percentages [(mol of each amino acid)/(mol of all amino acids) × 100] are presented along with their estimated integer values (in parentheses). Pseudomycins A–C were run in duplicate, pseudomycin D in triplicate, and syringomycin as a single sample. The mean total number of nanomoles of amino acids for each of these samples was 6.3, 3.7, 2.2, 7.6 and 19.1, respectively.
†Separate analyses were done to identify 3-hydroxyaspartic acid [3(OH)Asp]. Plus and minus signs signify the presence or absence, respectively, of this amino acid.

Structural Comparison of the Pseudomonad Antimycotics

Amino acid modifications may account for the unique but similar chromatographic, electrophoretic and mass spectrometric behavior of pseudomycins A–C. In syringomycin, for example, fatty acid esterification, chlorination, hydroxylation and/or dehydration of the peptide have been reported. The 16 Da difference between pseudomycins A and B could arise from esterifications with hydroxylated and unhydroxylated fatty acids, respectively. Similarly, pseudomycins A and C may contain fatty acids differing in length by two carbons (28 Da). The inability of composition analysis to identify all such structural differences is not surprising since modified amino acids can be altered or destroyed during acid hydrolysis or may produce PTC-amino acid derivatives which cannot be analyzed using the automated chemistry currently available.

Pseudomycins A–C share other characteristics of syringomycin and syringostatin A; for example being cyclic esters and amino-terminally N-acylated. Solvent and pH stability experiments have suggested this (Table 9), as have data from alkaline hydrolysis (Table 7). Additional support comes from the fact that automated Edman degradations have not yielded any useful sequence information from these pseudomycins. Amino-terminal pyroglutaminylation does not seem to explain this failure of the Edman chemistry, using the criterion that pyroglutamage aminopeptidase treatment does not result in successful sequence analysis.

The theoretical average masses of syringomycin and pseudomycin A may be calculated. The lactone of syringomycin contains, in addition to those residues quantified by amino acid analysis (Table 10), one each of 3(OH)Asp, 4-chlor-threonine, Dab and 3-hydroxydodecanoic acid, yielding a total mass of 1226.8 Da. If one postulates that pseudomycin A contains one each of 3(OH) Asp, 4-chlorothreonine and 3-hydroxydecanoic acid, in addition to those residues reported in Table 10, its lactone would have a total mass of 1224.8 Da. These masses agree, within 0.2 and 0.1 Da, respectively, with those actually observed (Table 9).

Plant Material

The sources of the plant material used for testing phytotoxic activity of the antimycotic are listed in Table 11. All plants were grown under controlled conditions with 8 hrs. of darkness at 28° C. and 16 hrs. of light at 32° C. per day.

TABLE 11

Sources of Plant Materials

| Common Name | Genera | Plant Material | Source |
|---|---|---|---|
| Corn | Zea | Seed | Burpee's |
| Rice | Oryza | Seed | Gary Strobel, MSU* |
| Wheat | Triticum | Seed | MSU seed lab |
| Sugarcane | Saccharum | Whole Plant | Gary Strobel, MSU |
| Timothy | Phleum | Seed | Doug Kenfield, MSU |
| Tall fescue | Festuca | Seed | Doug Kenfield, MSU |
| Crabgrass | Digataria | Seed | Doug Kenfield, MSU |
| Sunflower | Helianthus | Seed | Burpee's |
| Tomato | Lycopersicon | Seed | Burpee's |
| Cucumber | Cucumis | Seed | Burpee's |
| Geranium | Geranium | Whole Plant | Ernst's Home Center |
| Carob | Cerantonia | Seed | Tunisia |
| Crown of Thorns | Euphorbia | Whole Plant | Gary Strobel, MSU |
| Sicklepod | Cassia | Seed | Doug Kenfield, MSU |

*MSU—Montana State University

Assay for Phytotoxic Activity

Individual leaves were placed in a sterile petri dish and kept at high humidity by placing moist filter paper in the bottom of the dish. The solution to be assayed was dissolved in 0.05% TFA and applied to the leaf using a leaf puncture droplet overlay technique. An excised leaf was punctured using a Hamilton syringe, then a drop of the test sample was applied to the puncture wound. When testing partially purified pseudomycin from the acetone precipitation procedure, 1, 10, and 100 $\mu$g were applied. The control was 0.05% TFA and was applied in the same manner. Each petri dish was sealed with parafilm and incubated for a maximum of 4 days at room temperature, under light.

Fungal Strain Source

The source of the fungal strains used to test antimycotic activity are listed in Table 12.

TABLE 12

Fungal strain sources.

| Fungus | Source |
|---|---|
| Cephalosporium gramineum | Dr. Donald Mathre, MSU*, MT |
| Pyrenophora teres | Dr. Mike Bjarko, MSU, MT |
| Pyrenophora graminea | Dr. Mike Bjarko, MSU, MT |
| Rynchosporium secalis | Alfredo Martinez, MSU, MT |
| Ceratocystis ulmi | Dr. Gary Strobel, MSU |
| Rhizoctonia solani | ATCC 28268 |
| Botrytis alli | UCD 1159 |
| Sclerotinia sclerotiorum | Dr. David Sands, MSU |
| Verticillium dahliae | Dr. Donald Mathre, MSU, T-9 |
| Verticillium dahliae | Dr. Donald Mathre, MSU, SS-4 |
| Thielaviopsis basiola | Dr. Donald Mathre, MSU, CA |
| Fusarium oxysporum | ATCC E16322 |
| Fusarium culmorum | Bill Grey, MSU, MT |
| Fusarium graminearum | Bill Grey, MSU, MT |

*MSU—Montana State University

Assay for Antimycotic Activity Against Plant Pathogenic Fungi

Partially purified pseudomycin (after Amberlite XAD-2 column) was dissolved in 50% 1-propanol with 0.1% TFA at a concentration of 10 $\mu$g/$\mu$l. The solution (10 $\mu$l) was spotted onto the appropriate solid medium (Table 13) and allowed to dry. The solvent (10 $\mu$l) alone was spotted adjacent to the pseudomycin as a negative control. Each plate was oversprayed with a sterile water suspension of the fungus, sealed with parafilm, and incubated accordingly. Incubation time and temperature varied according to the fungus to be tested (Table 13).

TABLE 13

Growth conditions used for plant pathogenic fungi in the assay for antimycotic activity.

| Organism | Media | Temperature |
|---|---|---|
| Rynchosporium secalis | Lima Bean | 15° |
| Ceratocystis ulmi | PDA | 23° |
| Cephalosporium sp. | PDA | 23° |
| Pyrenophora teres | PDA-V8 | 15° |
| Pyrenophora graminea | PDA-V8 | 15° |
| Rhizoctonia solani | PDA | 23° |
| Botrytis alli | PDA | 23° |
| Sclerotinia sclerotiorum | modified CD | 23° |
| Verticillium albo-atrum | PDA | 23° |
| Verticillium dahliae | PDA | 23° |
| Thielaviopsis basicola | PDA | 23° |
| Fusarium oxysporum | Corn Meal | 23° |
| Fusarium graminearum | Corn Meal | 23° |
| Fusarium culmorum | Corn Meal | 23° |

TABLE 14

Pseudomycin Antimycotic Activity Towards Plant Pathogenic Fungi

| Fungus | Activity |
|---|---|
| Rynchosporium secalis | + |
| Ceratocystis ulmi | + |
| Cephalosporium gramineum | − |
| Pyrenophora teres | − |
| Pyrenophora graminea | − |
| Rhizoctonia solani | + |
| Botrytis allii | − |
| Sclerotinia sclerotiorum | + |
| Verticillium albo-atrum | + |
| Verticillium dahliae | + |
| Thielaviopsis basicola | + |
| Fusarium oxysporum | + |
| Fusarium graminearum | − |
| Fusarium culmorum | + |

Assay for Antibacterial Activity

The same screen as described for the fungi was used to test the antimycotic sensitivity of three plant bacterial pathogens; 1) Corynebacterium michigenese, a gram positive organism, 2) Xanthomonas campestris, a gram negative organism, and 3) P. syringae MSU 16H, the organism that produces the antimycotic. Pseudomycin (10 $\mu$l) was spotted onto Cory media for C. michigenense and King's B for X. campestris and syringae, at concentrations of 250, 25, 2.5, 0.25, and 0.025 $\mu$g/$\mu$l. They were then oversprayed with $\approx 2 \times 10^{11}$ org./ml and incubated at room temperature for 48 hours. Both X. campestris and C. michigenense were inhibited by a total of 2.5 mg and weakly inhibited by a total of 0.25 mg. These are relatively high concentrations required for inhibition. P. syringae was not inhibited by the antimycotic.

Phytotoxic Activity

Partially purified pseudomycin (from Amberlite XAD-2 column) was used to test phytotoxicity in a total of six different monocots and seven different dicots. One hundred, 10, and 1 $\mu$g of pseudomycin, dissolved in 0.05% TFA was applied to a puncture wound on the leaf surface. After incubation for four days at room temperature in a moist petri dish, the leaves generally developed zones of necrosis surrounded by an area of chlorosis. This is similar to the symptoms that develop with leaf blight. In addition to the monocots displayed brown runners and the dicots venal necrosis. All of the monocots were affected by the antimycotic. Three of the dicots were not affected at these concentrations; carob (Cerantonia), cucumber (Cucumis), and geranium (Geranium) (Table 15).

TABLE 15

Phytotoxicity of partially purified pseudomycin.

| | Amount Applied ($\mu$g) | | | | Amount Applied ($\mu$g) | | |
|---|---|---|---|---|---|---|---|
| Monocots | 100 | 10 | 1 | Dicots | 100 | 10 | 1 |
| Timothy | NCR | NCR | NCR | Sunflower | NC | NC | NC |
| | +++ | +++ | ++ | | ++ | ++ | + |
| Corn | NCW | NCW | NCW | Carob | -- | -- | -- |
| | +++ | +++ | ++ | | | | |
| Tall Fescue | GCR | GCR | GCR | Cucumber | -- | -- | -- |
| | +++ | +++ | ++ | | | | |
| Crabgrass | WNC | WNC | WNC | Tomato | NV | NV | -- |
| | +++ | +++ | ++ | | ++ | ++ | |
| Sugarcane | NR | NR | NR | Geranium | -- | -- | -- |
| | +++ | +++ | + | | | | |
| Wheat | NC | NC | NC | Crown of Thorns | NV | NV | NV |
| | +++ | +++ | + | | +++ | ++ | + |
| | | | | Sicklepod | NV | NV | NV |
| | | | | | +++ | ++ | + |

(N) = necrosis,
(C) = chlorosis,
(V) = vein necrosis,
(R) = brown runners,
(W) = water soaking,
(G) = green island.
The response was estimated to be weak (+),
moderate (++),
or severe (+++).
(-) = no difference relative to the control.

TABLE 16

Growth conditions used for plant pathogenic fungi in the assay for antimycotic activity.

| Organism | Media | Temperature |
|---|---|---|
| *Rynchosporium secalis* | Lima Bean | 15° |
| *Ceratocystis ulmi* | PDA | 23° |
| Cephalosporium sp. | PDA | 23° |
| *Pyrenophora teres* | PDA-V8 | 15° |
| *Pyrenophora graminea* | PDA-V8 | 15° |
| *Rhizoctonia solani* | PDA | 23° |
| *Botrytis alli* | PDA | 23° |
| *Sclerotinia sclerotiorum* | modified CD | 23° |
| *Verticillium albo-atrum* | PDA | 23° |
| *Verticillium dahliae* | PDA | 23° |
| *Thielaviopsis basicola* | PDA | 23° |
| *Fusarium oxysporum* | Corn Meal | 23° |
| *Fusarium graminearum* | Corn Meal | 23° |
| *Fusarium culmorum* | Corn Meal | 23° |

Antifungal chemotherapy is limited both in the number of available agents and in therapeutic applications. Many of the antifungal agents are toxic even at low concentrations. For example, Amphotericin B, used for the treatment of superficial Candida infections, is active in vitro at concentrations of 0.01–2 $\mu$g/ml. It is also highly toxic, and some impairment of renal function is seen in all patients regardless of dosage given. New chemicals are needed for human antifungal agents.

One of the requirements of a human antifungal agent is stability in blood serum. Pseudomycin remains active in blood serum.

In order to test the stability of pseudomycin in human serum, human whole blood was allowed to clot, then centrifuged at 4000 X G to separate the serum from the cells. Partially purified pseudomycin was suspended in the serum, in duplicate tubes, at concentrations of 50, 5, 0, 0.5, 0.05, and 0.005 $\mu$g/$\mu$l. The antimycotic was dissolved in water, at the same concentrations, for the control. One set of tubes was incubated for two days at room temperature and one set at 37° C. The antimycotic was tested for activity at 24 and 48 hours using Geotrichum as the assay organism. The pseudomycin remained active in both the serum mixtures and the control for the full 48 hours.

Furthermore, a partially purified preparation of pseudomycin is not endotoxic. This is especially important where the pseudomycin is used for intravenous treatment. In the situation wherein a human or animal patient is afflicted with a deep systemic infection, injection of the antimycotic is typically necessary for treatment. Endotoxins generally include the lipopolysacchrides from the cell walls of gram negative bacteria. When minute amounts of endotoxins are exposed to Linulus amoebocyte lysate, the lysate increases in viscosity and eventually gels. This is the basis of the Etoxate test. Three different samples were tested for the presence of endotoxin; 1) BuOH crude extract, 2) TLC eluate and, 3) Amberlite XAD-2 eluate. All glassware was soaked in a 4% solution of dimethyldichlorosilane, then rinsed thoroughly with double distilled water. The glassware was then heat cured at 100° C. overnight.

Twelve of the silanized tubes were prepared as indicated in Table 17. Each sample was mixed with amoebocyte lysate alone (Table 18, tubes A) to test for the presence of endotoxin. The samples were also mixed with lysate and a known amount of endotoxin standard (tubes B). The pseudomycin, water, and endotoxin standard dilutions were added first, followed by the E-toxate working solution. Each tube was mixed gently, then incubated for one hour undisturbed at 37° C. These tubes test for the presence of an inhibitor in the sample.

TABLE 17

Contents of tubes for the endotoxin assay.
All samples were dissolved in endotoxin freewater and adjusted to pH 6.5 with endotoxin free NaOH.

| Tubes | | Sample | |
|---|---|---|---|
| A | Tests for endotoxin in sample | 1 | BuOH crude extract |
| B | Tests for etoxate inhibitor in sample | 2 | eluted from TLC plate |

TABLE 17-continued

Contents of tubes for the endotoxin assay.
All samples were dissolved in endotoxin freewater and adjusted to pH 6.5 with endotoxin free NaOH.

C  Negative control                3  Amberlite XAD-2 column
D–H  Standard dillutions

| | Tubes | | | | | | | | | | |
|---|---|---|---|---|---|---|---|---|---|---|---|
| Contents | A1 | A2 | A3 | B1 | B2 | B3 | C | D | E | F | G | H |
| Sample | .1 ml | .1 ml | .1 ml | .1 ml | .1 ml | .1 ml | | | | | | |
| Water | | | | | | | .1 ml | | | | | |
| Endotoxin Standard | | | | .004 µg | .004 µg | .004 µg | | .008 µg | .004 µg | .002 µg | .001 µg | .0005 µg |
| Etoxate | .1 ml | .1 ml | .1 ml | .1 ml | .1 ml | .1 ml | .1 ml | .1 ml | .1 ml | .1 ml | .1 ml | .1 ml |

TABLE 18

Results of Etoxate test for endotosins.
All samples were dissolved in endotoxin freewater and adjusted to pH 6.5 with endotoxin free NaOH.

| Tubes | Sample |
|---|---|
| A  Tests for endotoxin in sample | 1  BuOH crude extract |
| B  Tests for etoxate inhibitor in sample | 2  eluted from TLC plate |
| C  Negative control | 3  Amberlite XAD-2 column |
| D–H  Standard dillutions | |

| | Tubes | | | | | | | | | | |
|---|---|---|---|---|---|---|---|---|---|---|---|
| Contents | A1 | A2 | A3 | B1 | B2 | B3 | C | D | E | F | G | H |
| Sample | .1 ml | .1 ml | .1 ml | .1 ml | .1 ml | .1 ml | | | | | | |
| Water | | | | | | | .1 ml | | | | | |
| Endotoxin Standard | | | | .004 µg | .004 µg | .004 µg | | .008 µg | .004 µg | .002 µg | .001 µg | .0005 µg |
| Etoxate | .1 ml | .1 ml | .1 ml | .1 ml | .1 ml | .1 ml | .1 ml | .1 ml | .1 ml | .1 ml | .1 ml | .1 ml |
| Results | – | – | – | – | + | – | – | + | + | + | + | + |

After incubation, the tubes were removed, one at a time, and slowly inverted 180° while observing for evidence of gelation. A positive test is the formation of a hard gel which permits complete inversion of the tube or vial without disruption of the gel. All other results were considered negative.

The BuOH crude extract and the eluate from the XAD-2 Amberlite column tested negative for endotoxin (tube A), but the corresponding tube B was negative. This means there is an inhibitor in the sample and the test is invalid. The sample from TLC tested negative for endotoxin and the inhibitor. This test indicates a certain level of purity required for applied use of this toxin. The minimum inhibitory concentration of the toxin against seven human fungal pathogens was estimated using a serial tube dilution technique. The toxin was most effective at inhibiting the yeast fungi, Candida and cryptococcus (Table 19).

TABLE 19

Minimal inhibitory concentrations of pseudomycin A
against fungal pathogens of humans.

| | MIC (µg ml$^{-1}$)* | | |
|---|---|---|---|
| Organism | 24 h | 48 h | 72 h |
| Candida albicans 89–80 | 3.12 | 25 | ND |
| Candida albicans 89–96 | 3.12 | 12.5 | ND |
| Candida tropicalis | 3.12 | 6.25 | ND |

TABLE 19-continued

Minimal inhibitory concentrations of pseudomycin A
against fungal pathogens of humans.

| | MIC (µg ml$^{-1}$)* | | |
|---|---|---|---|
| Organism | 24 h | 48 h | 72 h |
| Cryptococcus neoformans | 1.56 | 3.1 | ND |
| Bipolaris spicifera | ND | 12.5 | >50 |
| Aspergillus fumigatus | ND | 12.5 | 50 |

*MIC is defined as the minimal concentration required to cause an inhibition of fungal growth as judged by the turbidity of the broth suspension.

In order to test the minimum inhibitory concentrations for human fungal pathogens, the following was performed.

A serial dilution tube test was used in which the toxin was diluted out in tubes containing equal amounts of the fungus to be tested which were suspended in the appropriate medium. The tubes were incubated at room temperature or 30° C. for the mould fungi or yeast fungi, respectively. After incubation, the last tube in the dilution series which inhibited the growth of the fungi, was recorded as the minimum inhibitory concentration.

The following describes the methods and further characterization of the pseudomycins of the present invention.

Microbiological Methods

The P. syringae MSU 16H strain is an elm tree acclimated transposon (fn 903) generated mutant of the wild type strain MSU 174. It is equivalent to MSU strain 206 previously described in (Harrison et al., (1991), J. Gen. Microbiol. 137, 2857–2865). It was grown in still culture under conditions reported in (Ballio et al. (1990) FEBS Lett. 269; 377–380). Antifungal activity was assayed on *Rhodotorula pilmanae* (Sinder et al. (1991) Physiol. Plant Pathol. 1, 199–213).

Preparation of Pseudomycins

After 9–10 days growth at 25° C. the bioactive metabolites were extracted and partially purified according to Bidwai et al. (Bidwai et al. (1987) Plant Physiol. 83: 39–43), and finally fractionated by reverse phase HPLC on an Aquaspore RP300 column (4.6×250 mm, 7 μm ID. Applied Biosystems) using a Beckman System Gold 126 instrument under conditions described in (Iacohellis et al. (1992) Physiol. Mol. Plant Pathol. 40:107–116). Individual peaks were freeze-dried, quantitated by amino acid analysis after HCl hydrolysis, and assayed for activity toward *R pilimanae*.

Analytical methods

Amino acids were analyzed out as reported in (8) except that an Eppendorf-Biotronik LC 3000 analyzer was used. Some analyses were also performed by GC-MS after transformation into TBDMS derivatives (Chaves Das Neves et al. A.M.P. (1987) J. Chromatogr, 392, 249–258). The chirality of amino acid residues was determined by Marfey's method (Marfey, P. (1984) Carlsberg Res. Comm. 591–596). Peptide sequences were obtained by automated Edman degradation using an Applied Biosystems model 476A sequencer. Samples were spotted on Problott membrane (Applied Biosystems) and sequenced with a Blott Cartridge (Applied Biosystems).

Table 20 shows an amino acid comparison (integral values) for the pseudomycins using syringomycin as a comparison.

TABLE 20

Amino acid (integral values) for the pseudomycins using syringomycin as a comparison*

| Amino acid | Molar Percentage | | | |
|---|---|---|---|---|
| | Pseudo-mycin A | Pseudo-mycin B | Pseudo-mycin C | Syringo-mycin |
| Lysine | 11.0 (1) | 11.1 (1) | 11.1 (1) | 0.2 (0) |
| Aspartic acid | 14.1 (1) | 14.7 (1) | 16.0 (1) | 1.2 (0) |
| Serine | 14.6 (1) | 15.9 (1) | 15.5 (1) | 24.4 (2) |
| "arginine" (chlorothreonine)** | 10.6 (1) | 10.2 (1) | 12.2 (1) | 13.4 (1) |
| diaminobutyric acid phenylalanine and 2,3 dehydro 2 amino butyric acid | 38.2 (3) | 37.9 (3) | 36.5 (3) | 39.2 (3) |
| hydroxy aspartic acid*** | + (1) | + (1) | + (1) | + (1) |
| TOTAL RESIDUES | 8 | 8 | 8 | 7 |

*Each sample was hydrolyzed, derivatized and analyzed according to standard methods. The numbers in each column show the exact molar percentages of each amino acid that was recovered for each hydrolyzed sample.
**Chlorothreonine seems to have the same retention time as arginine
**Data impossible to obtain without the presence of a standard for comparison, an estimated residue amount is given.
NOTE:
Threonine, itself was not found by this analysis. It may have been destroyed by acid hydrolysis. It is an integral amino acid in the structure (see FIG. 1).

Given that there are technical problems in obtaining correct analytical data by amino acid analysis, the inventors set out to make a complete structural determination of pseudomycins A, B and C. They now used new, more highly sensitive techniques, including high resonance NMR. The data obtained by this, and other methods described below have provided the chemical structure of pseudomycins A, B and C. The new data, supplant earlier reported analytical methods because of their sensitivity and superiority. These methods have allowed for a determination of the complete structure of pseudomycins A, B and C. FAB-MS spectra were recorded on a VG ZAB 2 SF instrument equipped with a cesium gun operating at 25 kV 2pA. Samples dissolved in 5% acetic acid were directly loaded onto the probe tip coated with glycerol/thioglycerol 1:1.

NMR spectra were run at 27° C. on a Bruker AMX600 instrument operating at 600.13 MHz. Samples (1 mg) were dissolved in 0.8 ml of either $D_2O$ or $H_2O/D_2O$ 90:10, at pH 4.8. 2D NMR experiments were performed in the phase-sensitive mode with TPPI phase cycle (Marion, D. et al. (1983) Biochem. Biophys. Res. Comm. 113, 967,974) typically using 2K of memory for 512 increments. The number of scans were optimized in order to obtain a satisfactory signal-to-noise-ratio. Total Correlation experiments (TOCSY) were performed using the MLEV-17 spinlock composite pulse sequence (Braunschweiler et al. (1983) J. Magn. Reson, 53, 521–528; and Bax. A. et al. (1985) J. Magn. Reson. 65, 355–360) with a typical mixing time ranging from 60 to 120 ms (relayed) in order to observe either direct or remote connectivities. NOE dipolar correlated 2D spectra were obtained using the NOESY pulse sequence (Wuthrich et al. (1984) J. Magn. Reson 58, 370–388).

The mixing time for the magnetization exchanges ranged from 60 to 220 ms. Data were processed on a microVax II graphics workstation by the "TRITON" 2D NMR software of R. Boelsen and G. Vuister, kindly provided by prof. R. Kaptein of Utrecht University. FIDS were weighted by a sinebell apodization function shifted typically π/3 in both dimensions. In all homonuclear 2D experiments, a matrix 1024×1024 in the phase-sensitive mode was thus obtained with a digital resolution of ≈5 Hz/point. A baseline correction was carried out in both dimensions using a polynomial fit. $^{13}C$-$^1H$ heteronuclear correlations were obtained in the reverse-detection mode on the AMX600 BRUKER instrument (1K×512w).

Chemical Methods

The lactone ring hydrolysis was obtained by 3 h incubation at 37° C. with 50 mM ammonium bicarbonate.

Enzymatic hydrolyses

Lipodepsipeptides (250 μg) dissolved in 0.1M ammonium bicarbonate (15 μl) pH 8.0 were incubated at 37° C. for >h with TPCK trypsin (Worthington Biochemicals Co.) using an enzyme/substrate ratio of 1:30. After lyophilization the hydrolysis products were fractionated by HPLC as described under 2.2. Elution was performed with a solvent gradient obtained by mixing 0.2% TFA in water with 70% acetonitrile containing 0.2% TFA, flow rate 0.8 ml/min. The main peaks were freeze-dried and the samples were analyzed by FAB-MS and Edman degradation.

Figure 11:
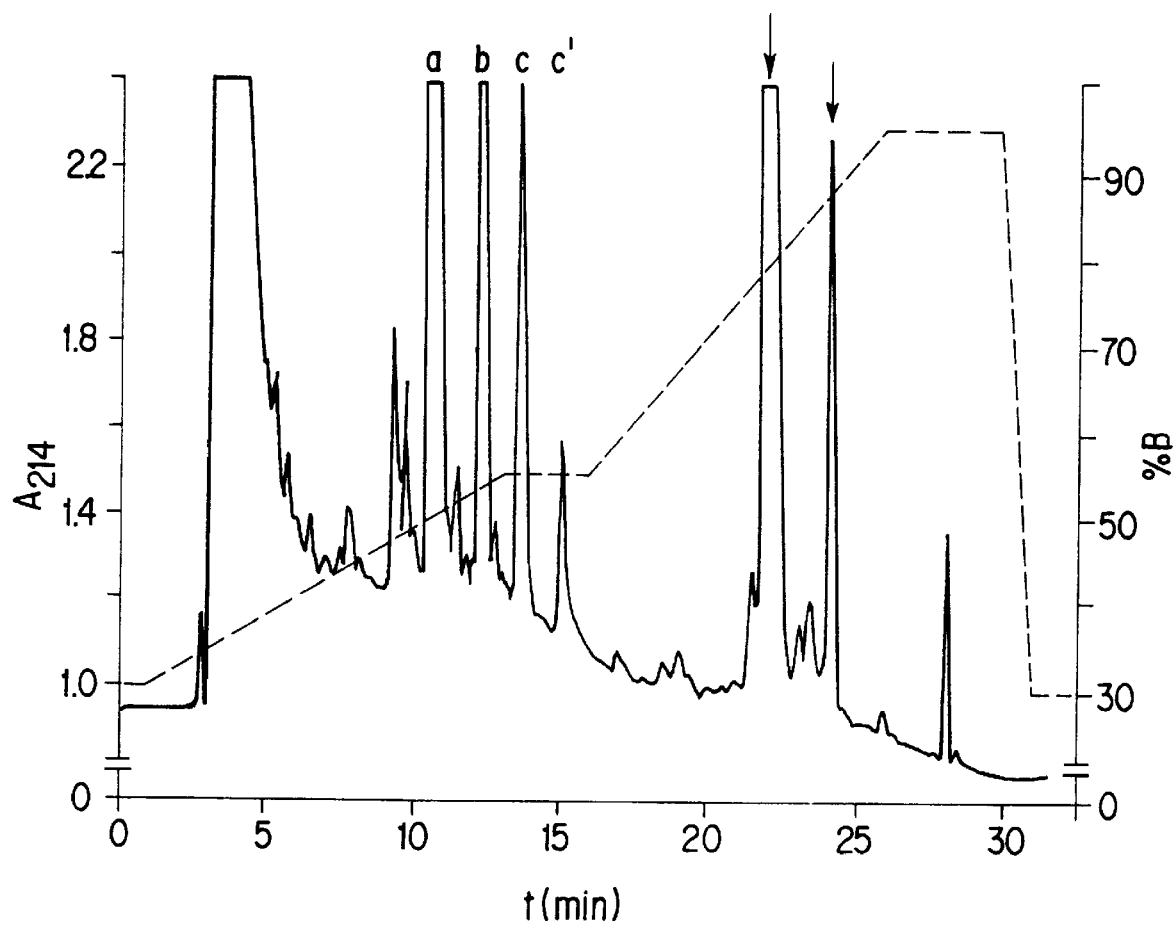
Figure 12:
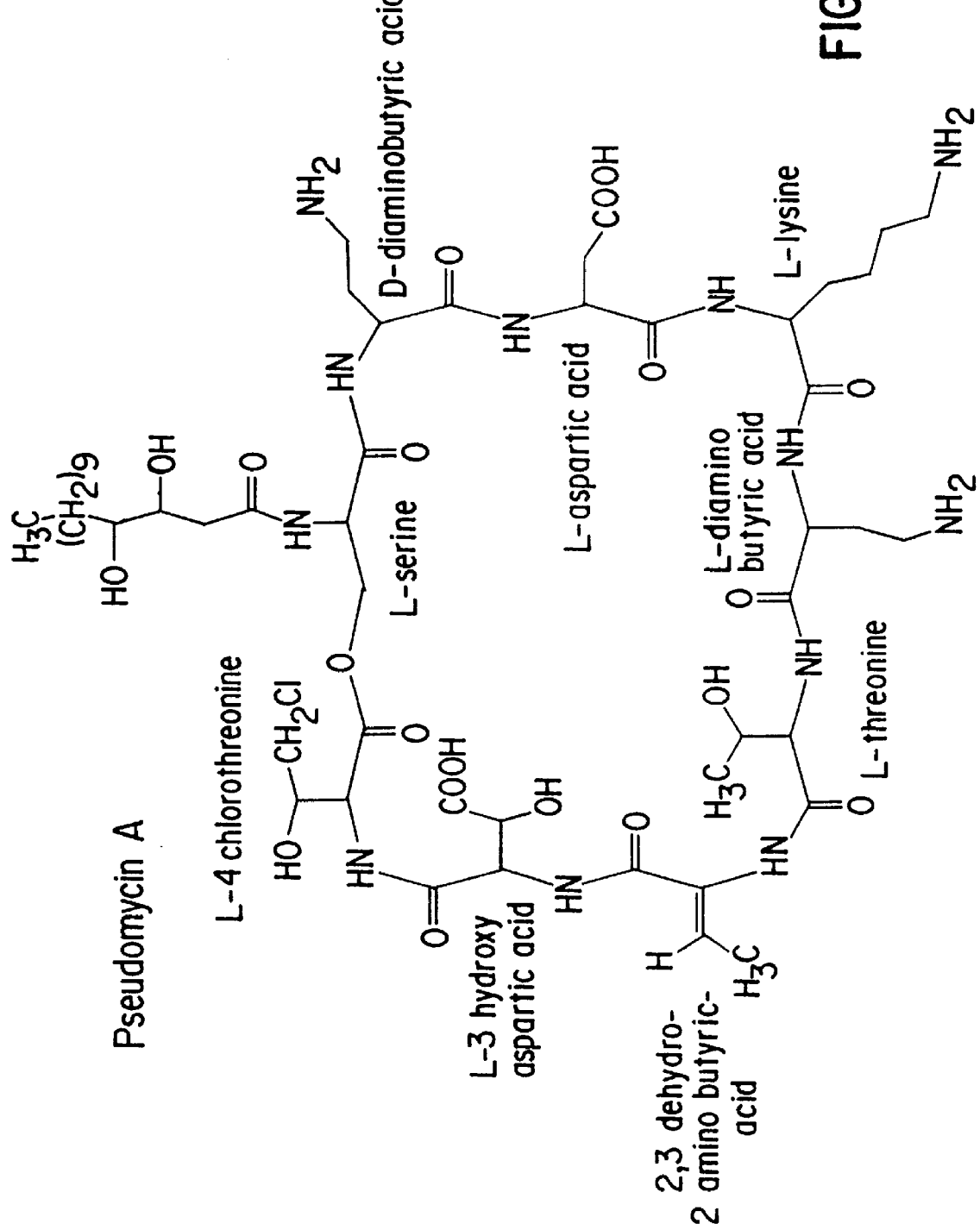

Reverse phase HPLC of a *P. syringae* MSU 16H extract partially purified according to Bidwai et al. (Bidwai et al. (1987) Plant Phsiol. 83: 39–43) produced an elution pattern of the same type observed with syringomycin and syringotoxin-producing strains (FIG. 11) (Ballio et al. (1991) FEBS Lett. 291: 109–112). Several peaks appeared in the region where the lipodepsinonapeptides are eluted, followed by two more hydrophobic peaks emerging from the column at higher acetonitrile-isopropanol concentration. FAB-MS and amino acid analyses (see below) of the substances isolated from the six more relevant peaks indicated that four corresponded to the previously described (Harrison et al., (1991), J. Gen. Microbiol. 137, 2857–2865) pseudomycin A, B, C and D, another (C') could be a further pseudomycin. (Harrison et al., (1991), J. Gen. Microbiol. 137, 2857–2865).

The amino acid composition (see below) clearly indicated that the substances isolated from peaks A, B, C and C' were different from known *P. syringae* metabolites. The identify of the two compounds from peaks D and D' with the two syringopeptins was proved by the same MH+ values, absorbance at 280 nm. HPLC elution times and detailed $^1$H-NMR data.

The complete structure of compounds contained in peaks A, B, C and C' was elucidated by the use of 2D NMR, FAB-MS and chemical and enzymatic degradations carried out on microquantities. Pseudomycin A, a relatively abundant component, was at first investigated. Amino acid determination, both by conventional ion-exchange chromatography and by GC-MS after derivatization with N-methyl-N-TBDMS-trifluoroacetamide (Chaves Das Neves et al. A.M.P. (1987) J. Chromatogr., 392, 249–258) showed the presence of one mole each of Ser, aThr, Asp, Asp(3-OH), Thr(4-Cl), Lys, and two moles of Dab.

The methods commonly used for 2D NMR studies reached the same conclusion and furthermore identified a Z-Dhb residue and the 3,4-dihydroxytetradecanoyl moiety; the chemical shifts and assignments of $^1$H and $^{13}$C-NMR spectra are reported in Table 21. All amino acid residues, with the exception of one Dab, had the L configuration.

TABLE 21

Structure of pseudomycins, syringostatins, syringotoxin and syringomycins.
Me(CH$_2$)$_n$—CH(X)—CH(OH)—CH$_2$—CO—L—Ser-
aa$_2$-aa$_3$-aa$_4$-aa$_5$-aa$_6$-Z—Dhb—L—Asp(3-OH)—L—Thr(4-Cl)

| | n | X | aa$_2$ | aa$_3$ | aa$_4$ | aa$_5$ | aa$_6$ |
|---|---|---|---|---|---|---|---|
| PSs A,C | 9,11 | OH | D—Dab | L—Asp | L—Lys | L—Dab | L—αThr |
| PSs B,C' | 9,11 | H | | | | | |
| SSs | 7,9 | H,OH | D—Dab | L—Dab | D—Hse | L—Orn | L—αThr |
| ST | 9 | H | D—Dab | Gly | D—Hse | L—Orn | L—αThr |
| SRs | 5,7,9 | H | D—Ser | D—Dab | L—Dab | L—Arg | L—Phe |

The presence in the molecule of nine amino acid residues and a long chain hydroxyacyl, the difference of 18 mass units between the calculated sum of the residues and the molecular weight found by FAB-MS (MH+ 1223–1225: the doublet indicates the presence of one chlorine atom), the observed addition of one mole of water (MH+ 1241–1243) by treatment with ammonium bicarbonate (followed by substitution of chlorine with OH:MH+ 1223 singlet), FAR-MS of a sample treated with ammonium bicarbonate produced a fragmentation pattern in agreement with the following partial sequence: Asp-Lys-Dab-aThr-Dhb-Asp(3-OH)-Thr(4-OH), where Thr(4-OH) arises from Thr(4-Cl) at basic pH. The occurrence of an L-lysine residue prompted to cleave pseudomycin A by trypsin.

After incubation with the enzyme the solution was fractionated by reverse phase HPLC. The fragment present in the main hydrophilic peak corresponded to the C-terminal part of the molecule, as ascertained by automated Edman degradation which yielded a Dab residue on the first cycle and a Thr residue on the second; the sequence determination was stopped in correspondence of the dehydro-amino acid (Wakamiya et al. (1985) Tetrahedron Lett. 26, 665–668).

Treatment of the same fragment by a modified Marfey's procedure (Marfey, P. (1984) Carlsberg Res. Comm. 591–596) allowed to assign the L-configuration to the Dab residue adjacent to Lys and consequently the D-configuration to the other Dab residue. The FAB-MS spectrum of a prominent more hydrophobic peak showed a pseudomolecular ion (MH+ 691) expected for the rest of the molecule, namely for 3,4-dihydroxytetradecanoyl-(Dab,Ser)-Asp-Lys-OH.

Figure 13:
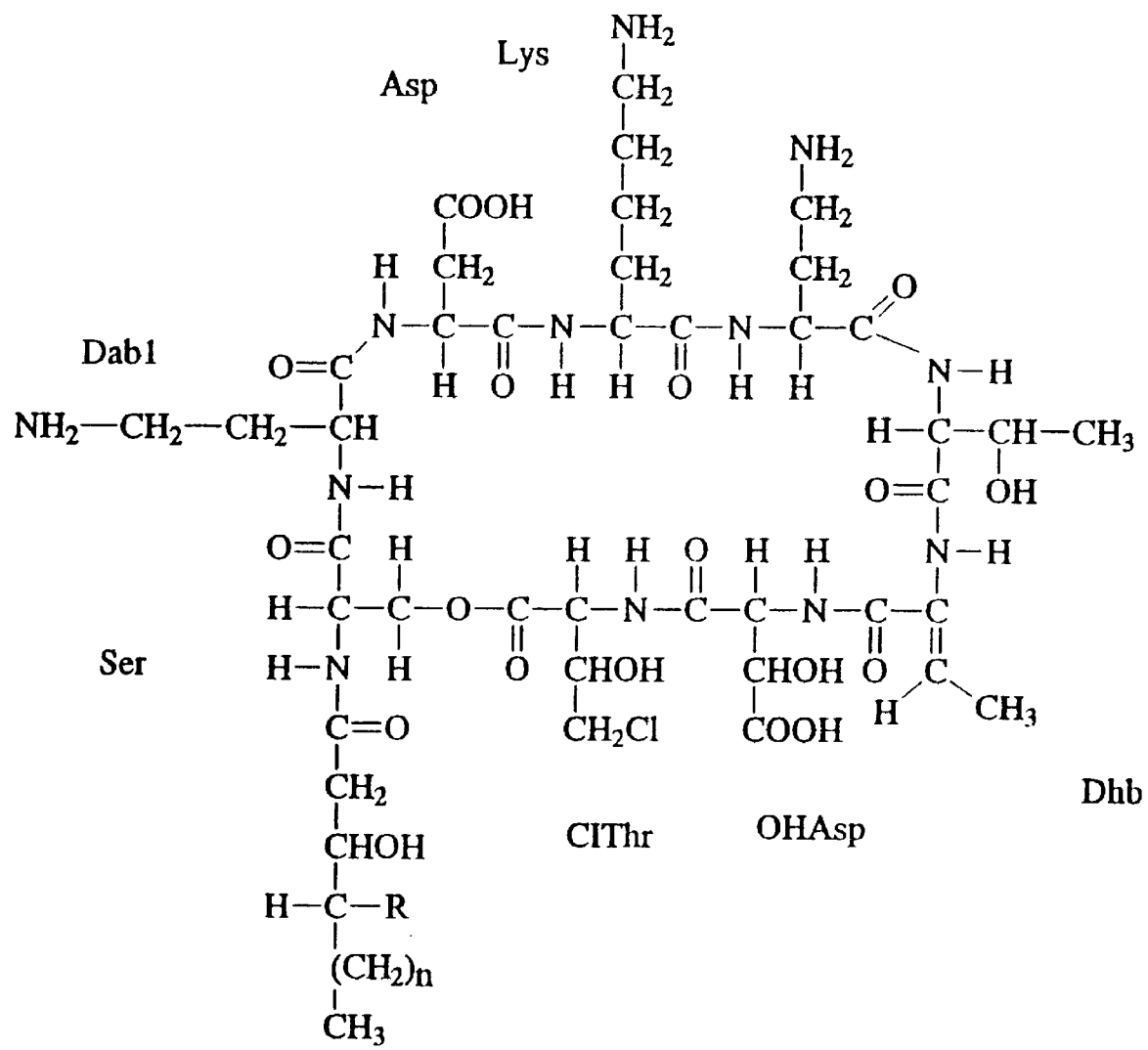
Figure 14:
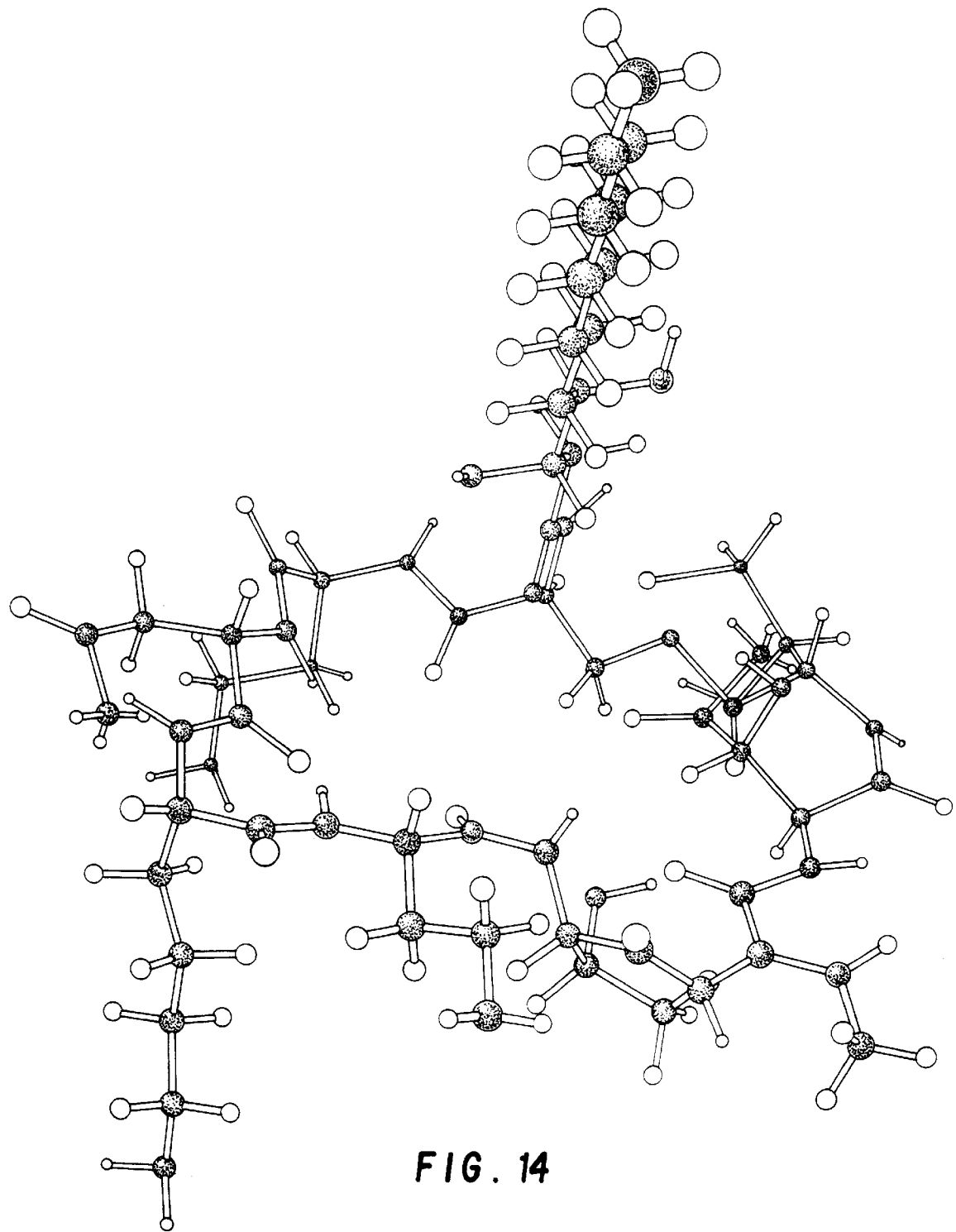
Figure 15:
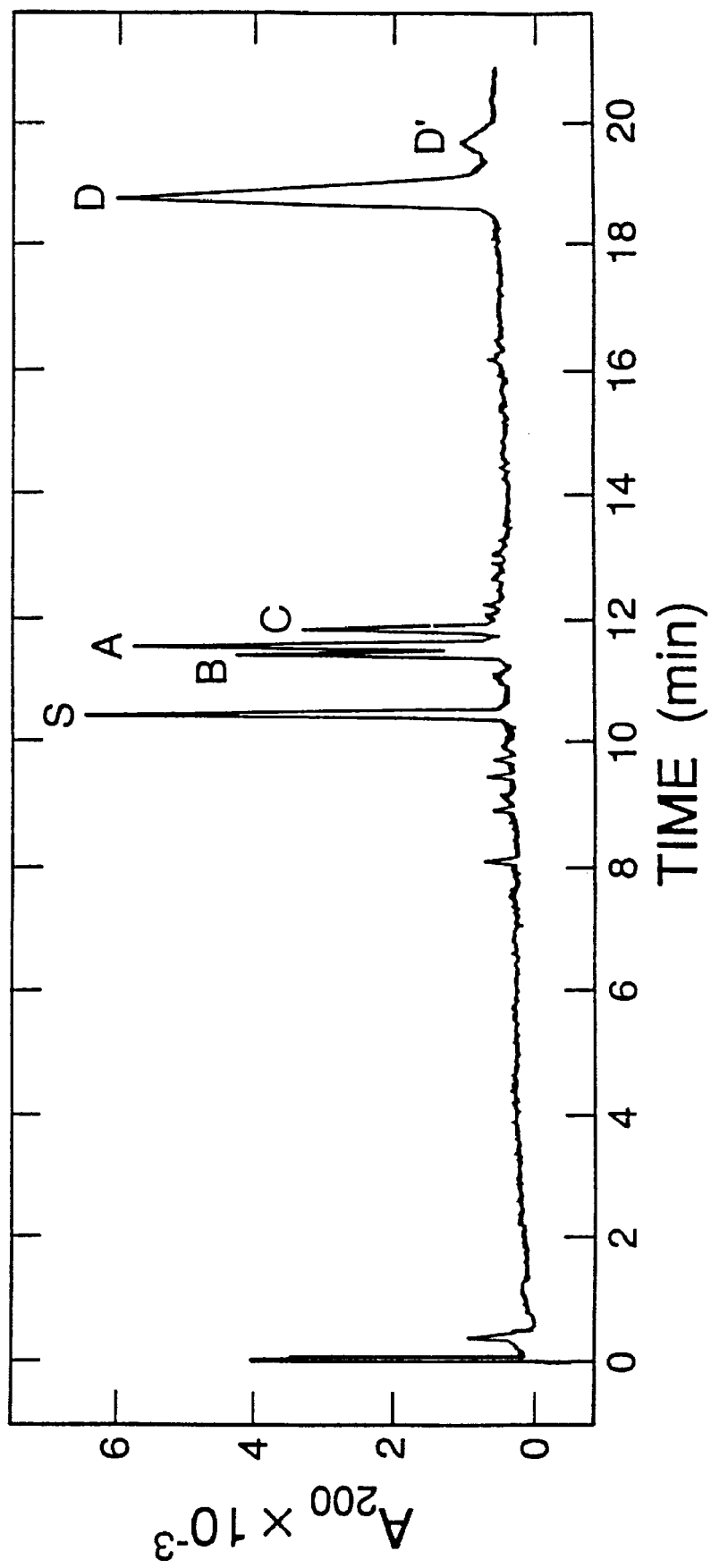

The complete sequence of the tetrapeptide moiety and the site of acylation emerged from NMR spectra of pseudomycin A (see Table 21). The complete structure of pseudomycin A is reported in FIG. 13, where the arrows indicate the short range strong NOE contacts which have allowed to elucidate, independently from the chemical approach, the amino acid sequence, as well as the position and the type of closure of the macro ring.

A number of long range NOE contacts have also been identified; these proximities, together with available information about the chirality of the amino acid residues, are prerequisites for the determination of the solution structure of this molecule.

Pseudomycins B(MH$^1$ 1207–1209), C (MH+ 1251–1253) and C'(MH+ 1235–1237) are closely related to pseudomycin A. In fact, amino acid composition, and fragmentation observed in the FAB-MS spectra after lactone opening with ammonium bicarbonate gave identical results for all four pseudomycins. Thus, very likely they differ only for the long chain acyl group: their MH+ values suggest that the nonapeptide moiety is acylated in pseudomycin B by 3-monohydroxytetradecanoate, a pseudomycin C by 3,4-dihydroxyhexadecanoate and in pseudomycin C' by 3-monohydroxyhexadecanoate. The position of the four pseudomycins in the reverse phase HPLC elution pattern is consistent with an increased hydrophobicity on passing from A to C'.

As compared to the known lipodepsinonapeptides from *P. syringae* pv. *syringae* (Table 21), the pseudomycins have: a) the same variety of fatty acids (3-hydroxy and 3,4-dihydroxy) previously found in syringostatins, except that some have a longer aliphatic chain (C$_{16}$); b) an identical N-terminal residue (L-Ser), N-acylated by the fatty acid and O-acylated by the terminal carboxyl group; c) the same C-terminal tripeptide with the carboxy group closing the lactone ring; d) a D-amino acid residue in the second position, similarly to all so far described congeners obtained for isolates of *P. syringae* pv. syringae (Scaloni et al. (1994) Nat. Product Lett. (in press)); e) the third and the fourth residues with the L-configuration, while in their congeners either one or the other has the D-configuration; f) the fifth residue correspondent to a basic L-amino acid residue (Dab), as found in syringomycins (Arg)(3,4) syringotoxin (Orn) (Ballio et al. (1990) FEBS Lett. 269; 377–380; and Fukuchi et al. (1990) Agric. Biol. Chem. 54; 3377–3379) syringostatins (Orn)(Isogai et al. (1990) Tetrahedron Lett. 31, 695–698).

The occurrence of L-Asp in the peptide moiety of the pseudomycins is a novel feature of the lipodepsinonapeptides which appears to affect their biological properties.

In sum, the invention provides for a composition for the treatment of fungal or bacterial infections comprising a substantially pure peptide pseudomycin derived from *P. syringae* MSU 16H and a pharmaceutical carrier, wherein the peptide comprises at least one peptide selected from the group consisting of proteins Pseudomycin A, Pseudomycin B and Pseudomycin C, each having a molecular weight (M+H+) of about 1224, 1208 and 1252 Da, respectively and mixtures of said proteins. (Actual mol weight 1223, 1207 and 1251 Da.) The composition may comprise one, two, three or all four peptides of the invention in any combination, including mixtures. Pseudomycins A and Pseudomycin C are particularly preferred. The peptide pseudomycin of the invention may also be synthetically produced.

Pseudomycin A, Pseudomycin B, and Pseudomycin C comprises 1-L-chlorothreonine, 1-L-serine, 1-D diaminobutyric acid, 1-L-aspartic acid, 1-L-lysine, 1-L-diaminobutyric acid, 1-L-threonine, 1-2,3-dehydro 2-aminobutyric acid and 1 L-3-hydroxy aspartic acid.

Many fungi cause opportunistic infections in immunologically compromised patients, such as those suffering from AIDS. The most common treatment currently available for these systemic mycoses is administration of the highly toxic antibiotic amphotericin B. Since pseudomycins retain their antimycotic activity in human serum and are non-toxic in mice, they may be used as an alternative to amphotericin B in the treatment of these diseases.

Formulations of the pseudomycin protein of the invention may include from 0.01% to 99% pseudomycin protein and from 99% to 0.01% inert pharmaceutically acceptable carrier. Such carriers are known as evidenced by *Remington's Pharmaceutical Sciences,* 18th ed. (1992) Mack Publishing Co., incorporated herein by reference in its entirety. The pseudomycins may be administered by any methods known in the art as evidenced by *Remington's Pharmaceutical Sciences*. Dosages may also be calculated by methods known in the art. As is known in the art, dosages are dependant upon the type of administration, with different dosages for topical, intravenus, intramuscular and oral administration.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A substantially pure pseudomycin obtained from a pseudomonas bacteria comprising the amino acid sequence:

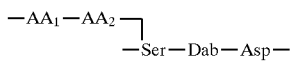

wherein
AA$_1$ is L-3-hydroxy-aspartyl;
AA$_2$ is L-4-chlorothreonyl;
Ser is L-serinyl;
Dab is D-diaminobutyryl; and
Asp is L-aspartyl;
and wherein the carboxyl group of AA$_2$ is bonded to the serinyl hydroxyl group via an ester linkage.

2. The pseudomycin according to claim 1, wherein said pseudomycin contains the following amino acids in an equimolar ratio: L-chlorothreonine, L-serine, D-diaminobutyric acid, L-aspartic acid, L-lysine, L-diaminobutyric acid, L-threonine, 2,3-dehydro-2-aminobutyric acid and L-3-hydroxy aspartic acid.

3. The pseudomycin according to claim 1, wherein said pseudomycin is isolated from *Pseudomonas syringae* MSU 16H (ATCC 67028).

4. The pseudomycin according to claim 1, wherein said pseudomycin contains a long chain fatty acid.

5. The pseudomycin according to claim 4, wherein said long chain fatty acid comprises an N-acylated serinyl derivative.

6. The pseudomycin according to claim 1, wherein said pseudomycin has substantially all of the antifungal characteristics of a pseudomycin derived from *Pseudomonas syringae* MSU 16H (ATCC 67028).

7. The pseudomycin according to claim 1, wherein said pseudomycin has substantially all of the antibacterial characteristics of a pseudomycin derived from *Pseudomonas syringae* MSU 16H (ATCC 67028).

8. A pharmaceutical antibiotic composition comprising an antibiotic-effective amount of at least one pseudomycin obtained from a pseudomonas bacteria comprising the amino acid sequence

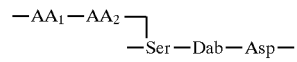

wherein
AA$_1$ is L-3-hydroxy-aspartyl;
AA$_2$ is L-4-chlorothreonyl;
Ser is L-serinyl;
Dab is D-diaminobutyryl;
Asp is L-aspartyl; and
wherein the carboxyl group of AA$_2$ is bonded to the serinyl hydroxyl group via an ester linkage; and a pharmaceutically acceptable carrier.

9. The pharmaceutical composition according to claim 8, wherein said pseudomycin has substantially all of the antifungal characteristics of a pseudomycin derived from *Pseudomonas syringae* MSU 16H (ATCC 67028).

10. The pharmaceutical composition according to claim 8, wherein said pseudomycin has substantially all of the antibacterial characteristics of a pseudomycin derived from *Pseudomonas syringae* MSU 16H (ATCC 67028).

11. The pharmaceutical composition according to claim 8, wherein said pseudomycin contains a long chain fatty acid.

12. The pharmaceutical composition according to claim 9, wherein said long chain fatty acid comprises an N-acylated serinyl derivative.

13. The pharmaceutical composition according to claim 8, wherein said composition comprises an effective amount of pseudomycin A, pseudomycin B, pseudomycin C, or a mixture thereof.

14. A method for treating a fungal infection comprising administering an effective amount of the pharmaceutical composition according to claim 8 to a patient in need thereof.

15. The method according to claim 14, wherein said patient is immunologically compromised.

16. A method for treating a bacterial infection comprising administering an effective amount of the pharmaceutical composition according to claim 8 to a patient in need thereof.

17. The method according to claim 16, wherein said patient is immunologically compromised.

18. An isolated, substantially pure Pseudomonas culture which produces at least one pseudomycin comprising the amino acid sequence

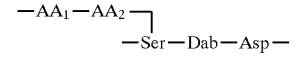

wherein
AA$_1$ is L-3-hydroxy-aspartyl;
AA$_2$ is L-4-chlorothreonyl;
Ser is L-serinyl;

Dab is D-diaminobutyryl;

Asp is L-aspartyl;

and the carboxyl group of $AA_2$ is bonded to the serinyl hydroxyl group via an ester linkage.

19. A process for the production of a pseudomycin comprising the amino acid sequence

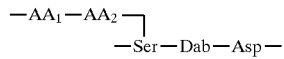

wherein $AA_1$ is L-3-hydroxy-aspartyl;

$AA_2$ is L-4-chlorothreonyl;

Ser is L-serinyl;

Dab is D-diaminobutyryl;

Asp is L-aspartyl;

and the carboxyl group of $AA_2$ is bonded to the serinyl hydroxyl group via an ester linkage, wherein said process comprises the steps:

(a) culturing a substantially isolated and pure Pseudomonas in a culture medium under conditions wherein said pseudomycin is produced, and (b) isolating said pseudomycin from said culture medium.

* * * * *